United States Patent
Gauguier et al.

(10) Patent No.: US 11,491,117 B2
(45) Date of Patent: Nov. 8, 2022

(54) COMPOUNDS FOR THE PREVENTION AND TREATMENT OF GLUCOSE INTOLERANCE RELATED CONDITIONS AND OBESITY

(71) Applicants: SORBONNE UNIVERSITÉ, Paris (FR); INSTITUT NATIONAL DE LA SANTE ET DE LA RECHERCHE MEDICALE (INSERM), Paris (FR); ASSISTANCE PUBLIQUE—HÔPITAUX DE PARIS, Paris (FR); KYOTO UNIVERSITY, Kyoto (JP)

(72) Inventors: Dominique Gauguier, Bures sur Yvette (FR); Fumihiko Matsuda, Kyoto (JP); François Brial, Villejuif (FR)

(73) Assignees: SORBONNE UNIVERSITÉ, Paris (FR); INSTITUT NATIONAL DE LA SANTE ET DE LA RECHERCHE MEDICALE (INSERM), Paris (FR); ASSISTANCE PUBLIQUE—HÔPITAUX DE PARIS, Paris (FR); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/652,947

(22) PCT Filed: Oct. 4, 2018

(86) PCT No.: PCT/EP2018/076958
§ 371 (c)(1),
(2) Date: Apr. 1, 2020

(87) PCT Pub. No.: WO2019/068788
PCT Pub. Date: Apr. 11, 2019

(65) Prior Publication Data
US 2020/0253889 A1 Aug. 13, 2020

(30) Foreign Application Priority Data
Oct. 4, 2017 (EP) .................................. 17306326

(51) Int. Cl.
*A61K 31/05* (2006.01)
*A61P 3/10* (2006.01)
*A61K 9/00* (2006.01)

(52) U.S. Cl.
CPC ................ *A61K 31/05* (2013.01); *A61P 3/10* (2018.01); *A61K 9/0019* (2013.01)

(58) Field of Classification Search
CPC combination set(s) only.
See application file for complete search history.

(56) References Cited

U.S. PATENT DOCUMENTS

| | | | | |
|---|---|---|---|---|
| 2010/0104548 A1* | 4/2010 | Rossetti | ............... | A61K 31/198 424/94.4 |
| 2011/0224260 A1* | 9/2011 | Kuo | .......................... | A61P 3/10 514/338 |
| 2015/0209383 A1* | 7/2015 | Boileau | .................. | A23L 33/26 514/58 |
| 2016/0347782 A1 | 12/2016 | Thiede et al. | | |

FOREIGN PATENT DOCUMENTS

| | | |
|---|---|---|
| EP | 0784981 A2 | 7/1997 |
| WO | 2016116054 A1 | 7/2016 |

OTHER PUBLICATIONS

Brial; Cell Reports 2020, 30, 2306-2320. doi: 10.1016/j.celrep.2020.01.066 (Year: 2020).*
Brial; Cell. Mol.Life Sci. 2018, 75, 3977-3990. doi: 10.1007/s00018-018-2901-1 (Year: 2018).*
Dufrasne; Current Medicinal Chemistry, 2011, 18, 3995-4011. doi: 10.2174/092986711796957301 (Year: 2011).*
Fujiwara; Free Radical Biology and Medicine 2011, 50, 883-891. doi: 10.1016/j.freeradbiomed.2010.12.033 (Year: 2011).*
Gezginci-Oktayoglu; Neuropeptides 2011, 45, 143-150. doi: 10.1016/j.npep.2011.01.001 (Year: 2011).*
Hanaoka; Experimental Neurology 1992, 115, 292-296. doi: 10.1016/0014-4886(92)90064-W (Year: 1992).*
Ho; Molecules 2017, 22, 90; 15 pages, doi: 10.3390/molecules22010090 (Year: 2017).*
Sameni; Cell Journal 2011, 13, 31-38. (Year: 2011).*
Wu; Diabetes, Metabolic Syndrome and Obesity: Targets and Therapy 2015, 8, 181-188. doi: 10.2147/DMSO.S82272 (Year: 2015).*
Yan; Drug Metabolism and Disposition 2005, 33, 1867-1876. doi: 10.1124/dmd.105.006387 (Year: 2005).*
Carrasco-Pozo; Experimental Cell Research 2015, 334, 270-282. doi:10.1016/j.yexcr.2015.03.021 (Year: 2015).*
Kim; European Journal of Pharmacology 569 (2007) 171-179. doi:10.1016/j.ejphar.2007.05.054 (Year: 2007).*
Manaharan; Food Chemistry 136 (2013) 354-363. doi: 10.1016/j.foodchem.2012.08.056 (Year: 2013).*
Gezginci-Oktayoglu; Apoptosis 2012,17, 14-24. DOI 10.1007/s10495-011-0657-2 (Year: 2012).*
Hamid; Journal of Functional Foods 2015, 16, 74-80. doi: 10.1016/j.jff.2015.04.011 (Year: 2015).*
Hirsch; The American Journal of Medicine 2004, 116 (3), Supp 1, 17-22. doi:10.1016/j.amjmed.2003.12.005 (Year: 2004).*
International Search Report dated Jan. 16, 2019, issued in corresponding International Application No. PCT/EP2018/076958, filed Oct. 4, 2018, 5 pages.
Written Opinion of the International Searching Authority dated Jan. 16, 2019, issued in corresponding International Application No. PCT/EP2018/076958, filed Oct. 4, 2018, 5 pages.

(Continued)

*Primary Examiner* — Daniel R Carcanague
(74) *Attorney, Agent, or Firm* — Christensen O'Connor Johnson & Kindness

(57) ABSTRACT

The disclosure pertains to a compound of formula (I), one of its pharmaceutically acceptable salts, or a composition comprising thereof, for use in the prevention or treatment of glucose intolerance related conditions, insulin deficit related conditions, nonalcoholic fatty liver disease and/or obesity.

8 Claims, 48 Drawing Sheets

(56) References Cited

OTHER PUBLICATIONS

Chang, W-C. et al.: "Protective Effect of Vanillic Acid against Hyperinsulinemia, Hyperglycemia and Hyperlipidemia via Alleviating Hepatic Insulin Resistnce and Inflammation in High-Fat Diet (HFD)-Fed Rats", Nutrients, (7)12, p. 9946-9959, Dec. 2015, XP055456648.

Ablat, A. et al.: "Antidiabetic effects of Brucea javanica seeds in type 2 diabetic rats", BMC Complementary and Alternative Medicine, (17)1, pp. 1-14, Feb. 2017, XP021239675.

Hanaoka, Y. et al.: "The therapeutic effects of 4-methylcatechol, a stimulator of endogenous nerve growth factor synthesis, on experimental diabetic neuropathy in rats" Journal of Neurological Sciences, Elsevier Scientific Publishing Co, (122)1, pp. 28-32, Mar. 1994, XP024401845.

Furukawa, S. et al.: "Stimulation of neurotrophin synthesis by 4-methylcatechol: a promising approach for neuroprotection" Bio-Medical Reviews, (10)0, p. 45, Mar. 2014, XP055456693.

Mohammed, A. et al.: "Ethyl acetate fraction of Aframomum meleguetafruit ameliorates pancreatic [beta]-cell dysfunction and major diabetes-related parameters in a type 2 diabetes model of rats" Journal of Ethnopharmacology, (175), Oct. 2015, pp. 518-527, XP029331835.

* cited by examiner

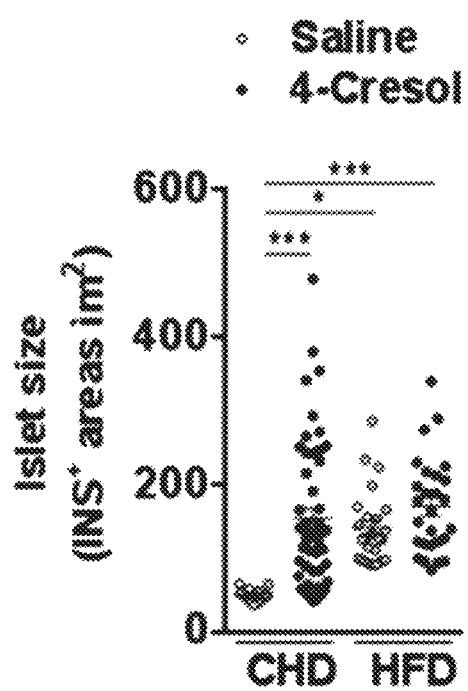 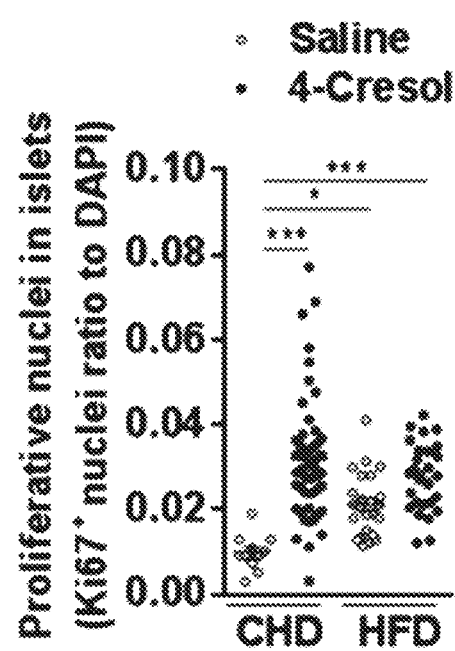
*FIG. 7B*  *FIG. 7C*

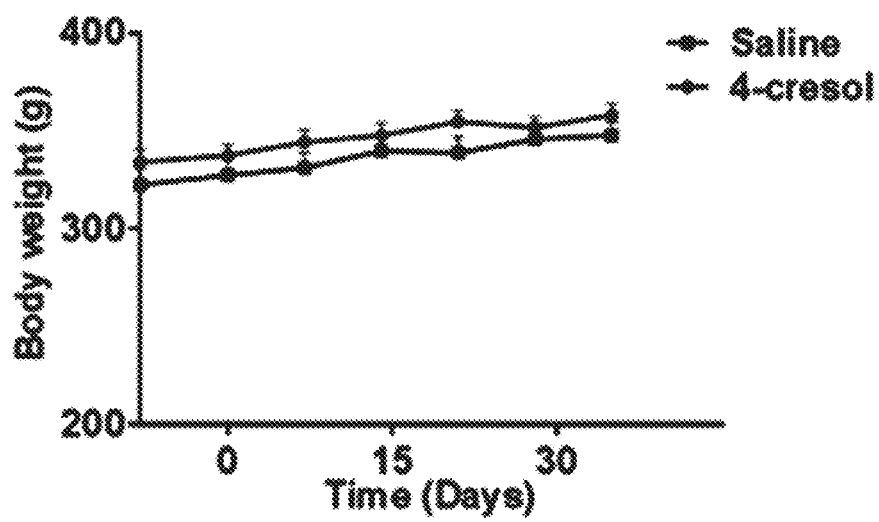
FIG. 8A
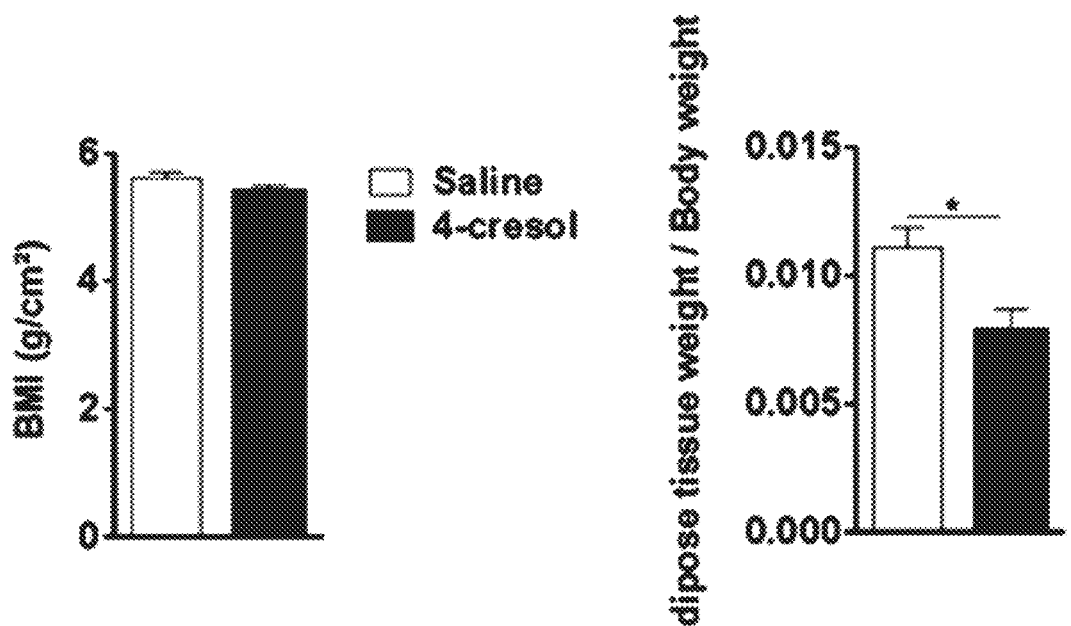
FIG. 8B
FIG. 8C

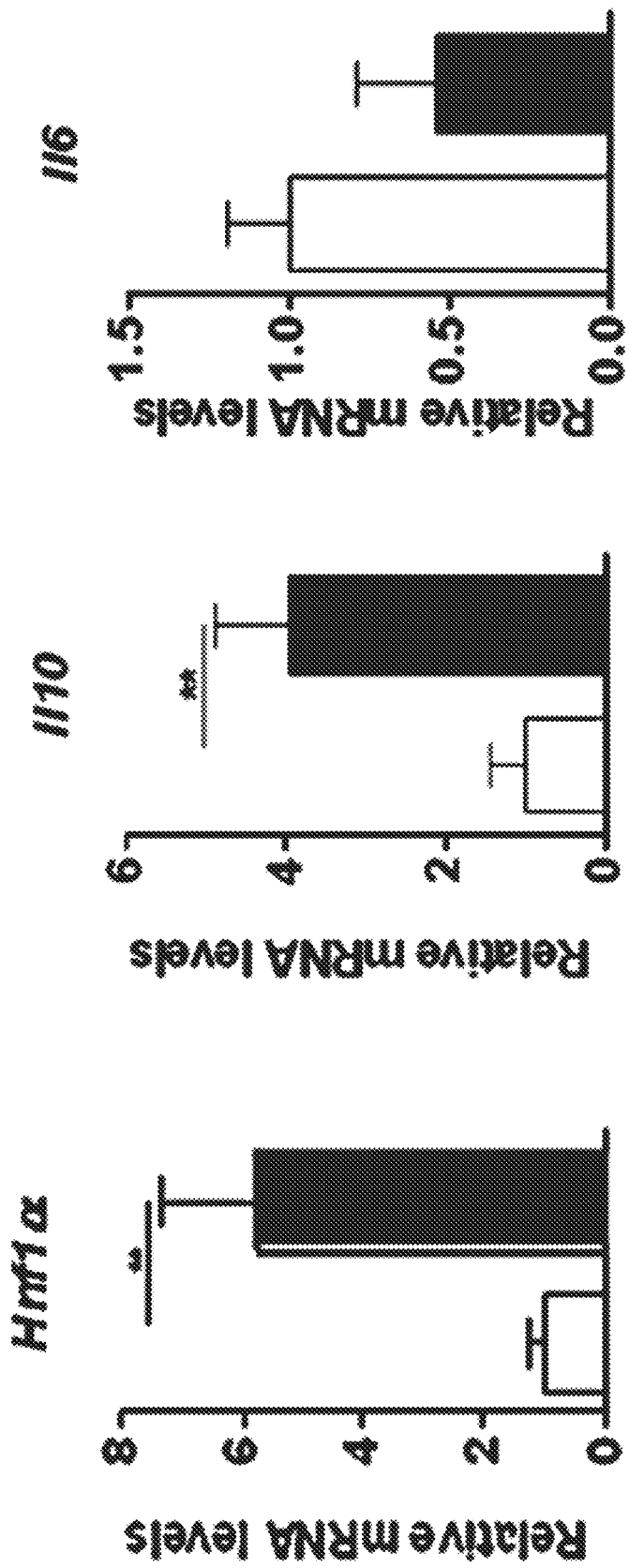

COMPOUNDS FOR THE PREVENTION AND TREATMENT OF GLUCOSE INTOLERANCE RELATED CONDITIONS AND OBESITY

The disclosed subject matter pertains to the field of compounds and methods for the treatment of metabolic disorders, in particular glucose intolerance related conditions, insulin deficit related conditions, nonalcoholic fatty liver disease and obesity.

PRIOR ART

In healthy individuals, plasma glucose levels are maintained within a narrow range, wherein both insulin-dependent and insulin-independent processes contribute to fasting and postprandial plasma glucose regulation.

Obesity and conditions related to glucose intolerance, such as diabetes mellitus, are all characterized by impaired insulin and glucose metabolism. Obesity is often associated with hyperinsulinemia and insulin resistance (a decrease in sensitivity to insulin), with a progressive decrease in insulin secretory function. Diabetes mellitus is characterized by a defect in insulin secretion or insulin resistance. Both result in elevated fasting blood glucose, which over time causes blood vessel and nerve damage, as well as liver damages such as liver fibrosis and abnormal fat liver content.

Historically, the therapy available for advanced stages of diabetes mainly consisted in insulin injection. However, this regular insulin injection presents with important adverse effects, such ashypoglycemic episodes, loss or overgrowth of fat tissue at injection sites, allergic reactions, and insulin resistance. Recently, more advanced therapies such as β-cells or stem cells transplantation have been developed which aim at augmenting or replacing insulin injections by increasing the number, or enhancing the function, of endogenous insulin-producing β-cells. However, besides ethical issues, technical and safety challenges in stem cell isolation, maintenance, expansion, donor-recipient matching and transplantation limit the efficacy of these strategies.

In type 2 diabetes associated with insulin resistance, insulin injection may not prove sufficient and the use of compounds capable of improving the sensitivity of body tissues to insulin, such as metformin or thiazolidinediones, may be necessary. However, nausea and diarrhea are possible side effects of metformin, and thiazolidinediones have been linked to weight gain and other more-serious side effects, such as an increased risk of heart failure and fractures. Because of these risks, these medications generally aren't a first-choice treatment.

Accordingly, there is a need for safe, effective compounds and treatment methods for metabolic disorders, in particular glucose intolerance related conditions and obesity.

BRIEF DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIGS. 7A-7E show the effects of chronic treatment of mice by 4-cresol on pancreas cell proliferation and vascularization.

FIGS. 8A-8E show the effects of chronic administration of 4-cresol in vivo in Goto-Kakizaki (GK) rats on body weight and organ weight.

DESCRIPTION

Figure 1A:
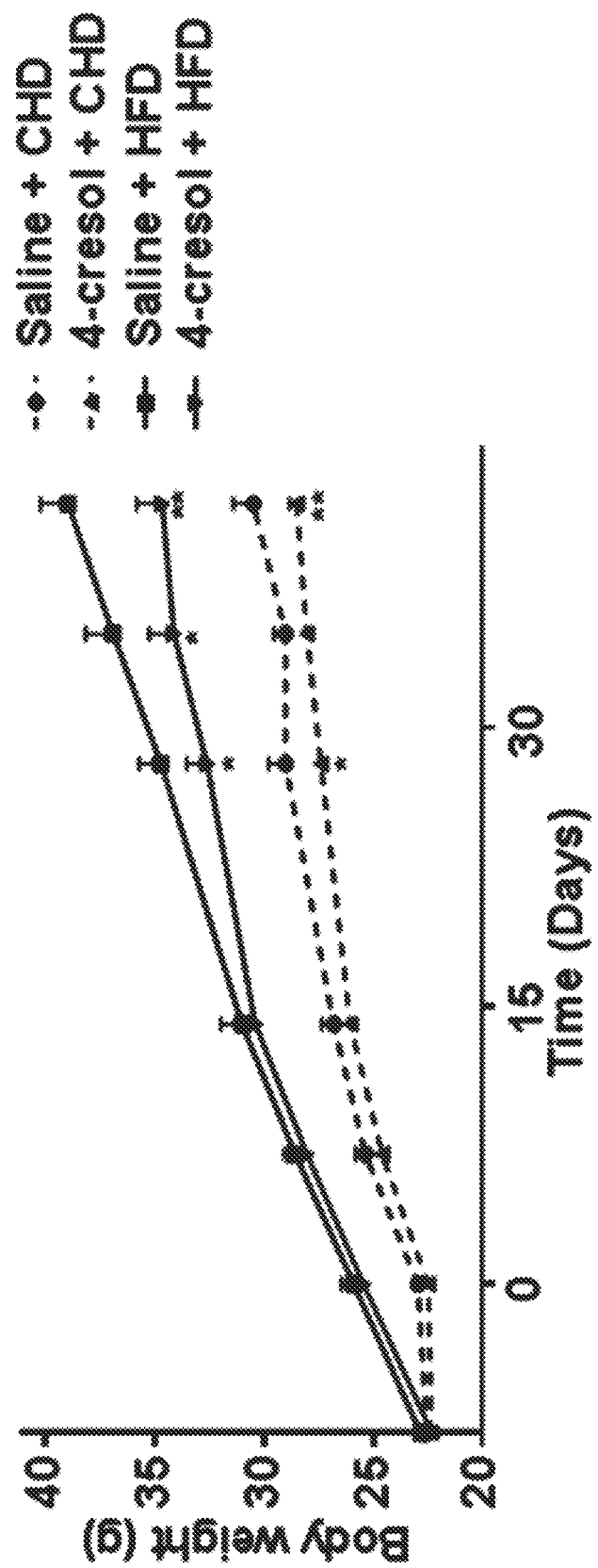
FIGS. 1A-1K show the impact of chronic administration of 4-cresol on body growth and glucose homeostasis.

Architectural changes in the gut microbiome are documented in human diabetes (Qin et al., 2012) and obesity (Le Chatelier et al., 2013) and there is growing interest in understanding how structural changes in gut bacterial communities affect host genome function and metabolism (Hansen et al., 2015; Nicholson et al., 2005).

In a previous study, the inventors were able to demonstrate significant correlations between coronary artery disease (CAD) risk factors and 4-cresol, a product of colonic fermentation of tyrosine and phenylalanine (Cummings, 1983).

Further to the above initial findings, the inventors have surprisingly found that treatment with 4-cresol and compounds derived there from results in significant reduction of body weight and adiposity, improved glucose homeostasis, and enhanced glucose-stimulated insulin secretion in vivo, even when the subjects were fed with a high fat diet during treatment.

Analysis of the underlying molecular phenomenon showed that the administration of said compounds reduced liver fibrosis and liver fat content, and increased both islet density and insulin positive area in treated subjects, thereby increasing pancreas weight, independent of the type of diet followed during treatment.

This supports the hypothesis that these compounds are useful in the prevention and/or treatment of insulin-related condition, in particular by enhancing glucose-stimulated insulin secretion. Further, since the secretion of insulin was found to be strictly glucose-dependent, there is little risk, if any, of hypoglycemic episodes.

The disclosed subject matter pertains to a compound of formula (I)

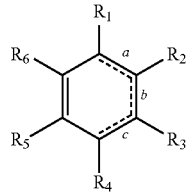

(I)

wherein
R₁ represents:
  a C1-C4 alkyl group, preferably —CH₃;
  a =CH₂ group, optionally substituted with a C1-C4 alkyl group;
  a group of formula —(CH₂)$_p$—C(=O)—X, optionally substituted with COOH, wherein p is 0, 1, 2 or 3 and X represents H, OH or COOH, said group being preferably —COH, —COOH, —CH₂—COOH, —CH₂—C(=O)—COOH or —CH₂—CH(COOH)—CH₂—COOH,
R₂ represents H or CH₃;
R₃ represents —H, —OH, or =O;
R₄ represents —OH, or =O;
R₅ represents —H or —CH₃; and
R₆ represents —H, or —CH₃,
a, b and c independently from each other represent a single or double bond, providing that:
  when R₁ represents an optionally substituted =CH₂ group, then a and c represent a single bond, b represents a double bond, R₃ is not =O and R₄ is =O;
  when R₁ is not an optionally substituted =CH₂ group, then:
    a and c represent a double bond, b represents a single bond, R₃ and R₄ are not =O; or
    a represents a double bond, b and c represent a single bond, R₃ and R₄ are =O;
one of its pharmaceutically acceptable salts, or a composition comprising thereof, for use in the prevention or treatment of glucose intolerance related conditions, insulin deficit related conditions, nonalcoholic fatty liver disease and/or obesity.

In the context of the present invention, the term "pharmaceutically acceptable" refers to molecular entities and compositions which have no toxic effect when administered to humans. When used herein, the terms "pharmaceutically acceptable salts" of a compound refers to the salts defined here and which possess the pharmacological activity of the parent compound. Such salts generally include salts of alkali metals, preferably potassium or sodium salts, salts of alkaline earth metals, preferably calcium, magnesium, or barium salts, ammonium salts or salts of organic bases such as aliphatic and aromatic amines, aliphatic diamines, hydroxy alkamines, and the like, preferably pyridinium salts or salts derived from methylamine, diethylamine, ethylenediamine, cyclohexylamine, ethanolamine and the like.

In a preferred embodiment, the compound of formula (I) for its use according to the invention as mentioned above is one in which:
R₁ represents:
  —CH₃;
  =CH₂;
  —COH;
  —CH2-CO—COOH;
  —COOH
  —CH2-CH(COOH)—CH2-COOH;
R₂ represents H;
R₃ represents —H, CH₃, —OH, or =O;
R₄ represents —OH;
R₅ represents —H, —OH; and
R₆ represents —H, or —CH₃.

Yet preferably, the compound of formula (I) is chosen in the list of compounds disclosed in table I below, that is to say the compound of formula (I) is chosen in the list consisting of p-cresol/4-cresol, 4-methylcatechol, 4-5 methyl hydroquinone, 6-5 methyl hydroquinone, 3-5 methyl hydroquinone, 4-quinone methide, 4-methyl ortho benzoquinone, 4-hydroxybenzylsuccinate, 4-hydroxybenzoate, 3,4-hydroxybenzoate, 4-hydroxybenzaldehyde, p-hydroxyphenyl pyruvic acid, p-hydroxyphenyl acetate, 3,4-hydroxyphenyl acetate.

Advantageously, the compound of formula (I) is 4-cresol or 4-methylcatechol.

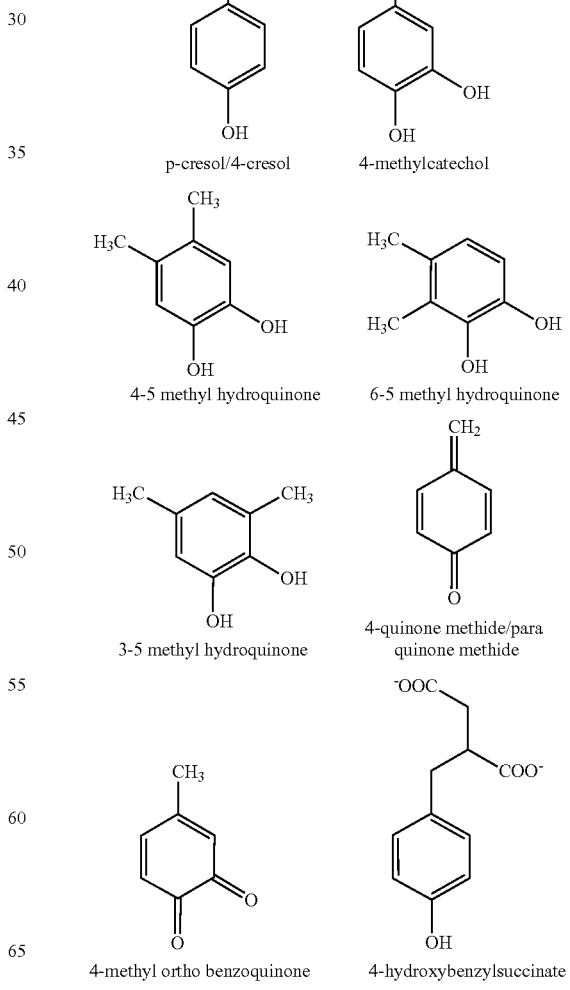

-continued

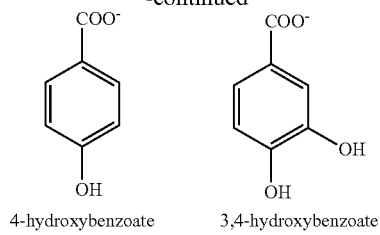

4-hydroxybenzoate    3,4-hydroxybenzoate

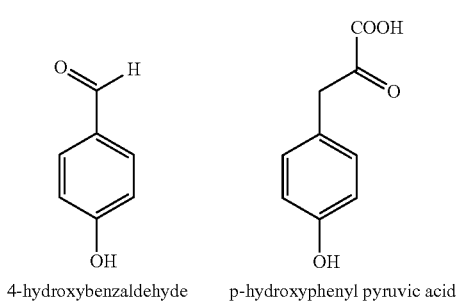

4-hydroxybenzaldehyde    p-hydroxyphenyl pyruvic acid

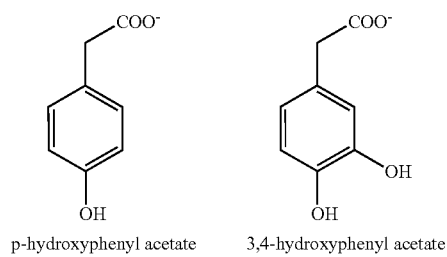

p-hydroxyphenyl acetate    3,4-hydroxyphenyl acetate

In a particular embodiment, the invention pertains to a compound of formula (I-1)

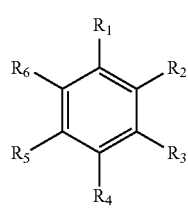

wherein $R_1$ represents:
- a C1-C4 alkyl group, preferably —$CH_3$;
- a group of formula —$(CH_2)_p$—C(=O)—X, optionally substituted with COOH, wherein p is 0, 1, 2 or 3 and X represents H, OH or COOH, said group being preferably —COH, —COOH, —$CH_2$—COOH, —$CH_2$—C(=O)—COOH or —$CH_2$—CH(COOH)—$CH_2$—COOH, $R_3$ represents —H, or —OH;

$R_4$ represents —OH;

$R_2$, $R_5$ and $R_6$ being as defined above.

In a particular embodiment, the invention pertains to a compound of formula (I-2)

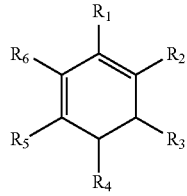

wherein $R_1$ represents:
- a C1-C4 alkyl group, preferably —$CH_3$;
- a group of formula —$(CH_2)_p$—C(=O)—X, optionally substituted with COOH, wherein p is 0, 1, 2 or 3 and X represents H, OH or COOH, said group being preferably —COH, —COOH, —$CH_2$—COOH, —$CH_2$—C(=O)—COOH or —$CH_2$—CH(COOH)—$CH_2$—COOH, $R_3$ represents =O;

$R_4$ represents =O;

$R_2$, $R_5$ and $R_6$ being as defined above.

In a particular embodiment, the invention pertains to a compound of formula (I-3)

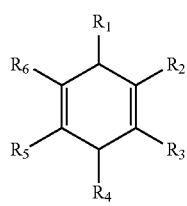

wherein $R_1$ represents a =$CH_2$ group, optionally substituted with a C1-C4 alkyl group;

$R_3$ represents —H or —OH, preferably —H;

$R_4$ represents =O;

$R_2$, $R_5$ and $R_6$ being as defined above.

Preferably, the invention pertains to the compound of formula (I) for its use according to the invention as mentioned above is one in which:

$R_1$ represents:
- —$CH_3$;
- =$CH_2$;
- —COH;
- —$CH_2$—CO—COOH;
- —COOH; or,
- —$CH_2$—CH(COOH)—$CH_2$—COOH;

$R_2$ represents —H or —$CH_3$;

$R_3$ represents —H, —OH, or =O;

$R_4$ represents —OH, or =O;

$R_5$ represents —H, —$CH_3$; and $R_6$ represents —H or —$CH_3$.

The disclosed subject matter further pertains to a method of treating or preventing glucose intolerance related conditions, insulin deficit related conditions, nonalcoholic fatty liver disease and/or obesity in a subject, comprising administering to said subject at least one of the compounds of formula (I), one of its pharmaceutically acceptable salts, or a composition comprising thereof.

In the context of the invention, glucose intolerance related conditions include:
- pre-diabetes, in particular pre-diabetes with impaired fasting glucose and pre-diabetes with impaired glucose tolerance,
- insulin-dependent diabetes mellitus (type 1 diabetes mellitus),
- non-insulin-dependent diabetes mellitus (type 2 diabetes mellitus),
- gestational diabetes mellitus,
- other specific types of diabetes mellitus, as herein defined.

In an embodiment, the glucose intolerance related condition is insulin-dependent diabetes mellitus (type 1 diabetes mellitus).

Preferably, the glucose intolerance related condition is insulin-dependent diabetes mellitus (type 1 diabetes mellitus)

In the context of the invention, the terms "glucose intolerance" are to be construed as generally defined in the field, that is to say as either impaired fasting glucose (IFG) or impaired glucose tolerance (IGT). According to the World Health Organisation's definitions for IFG and IGT, glucose intolerance is defined as: a fasting blood glucose level of above 6.0 mmol/L or a blood glucose level of over 7.8 mmol/L 2 hours after consuming 75 g of glucose. A number of tests can be used to diagnose glucose intolerance, including the fasting plasma glucose test and the oral glucose tolerance test (OGTT).

In the context of the invention, the terms "insulin deficit related conditions" include various forms of pancreatitis, comprising for instance acute pancreatitis and chronic pancreatitis. In the context of the invention, the term "pancreatitis" refers to inflammation of the pancreas. Usually, symptoms of pancreatitis include pain in the upper abdomen, nausea and vomiting. In acute pancreatitis a fever may occur and symptoms typically resolve in a few days. In chronic pancreatitis weight loss, fatty stool, and diarrhea may occur. Complications may include infection, bleeding, diabetes mellitus, or problems with other organs.

In the context of the invention, the terms "nonalcoholic fatty liver disease" are to be construed as generally defined in the field, that is to say as a type of fatty liver which occurs when fat is deposited (steatosis) in the liver due to causes other than excessive alcohol use. Usually, elevated liver enzymes and a liver ultrasound showing steatosis are symptoms associated with the diagnosis of nonalcoholic fatty liver disease.

In the context of the invention, the term "obesity" is to be construed as generally defined in the field, that is to say as a medical condition in which excess body fat has accumulated to the extent that it may have an adverse effect on health. In Caucasian populations, it is typically defined by a body mass index (BMI)≥30 kg/m². Further, in Caucasian populations, the following classification is typically applied:
- Any BMI≥35 or 40 kg/m² is defined as severe obesity.
- A BMI of ≥35 kg/m² and experiencing obesity-related health conditions or ≥40-44.9 kg/m² is defined as morbid obesity.
- A BMI of ≥45 or 50 kg/m² is defined as super obesity.

In the context of the invention, the term "pre-diabetes" is to be construed as generally defined in the field, that is to say as the precursor stage before diabetes mellitus in which not all of the symptoms required to diagnose diabetes are present, but blood sugar is abnormally high. Two main types of pre-diabetes have been described, impaired fasting glucose (IFG) and impaired glucose tolerance. In the context of the invention, "pre-diabetes with impaired fasting glucose (IFG)" is defined according to the World Health Organization (WHO) criteria, that is to say as a fasting plasma glucose level from 6.1 mmol/l (110 mg/dL) to 6.9 mmol/L (125 mg/dL). In the context of the invention, "pre-diabetes with impaired glucose tolerance" is defined according to the World Health Organization (WHO) criteria, that is to say two-hour glucose levels of 140 to 199 mg per dL (7.8 to 11.0 mmol/1) on the 75-g oral glucose tolerance test.

In the context of the invention, the terms "type 1 diabetes mellitus" are to be construed as generally defined in the field, that is to say by absolute insulin deficiency.

In the context of the invention, the terms "type 2 diabetes mellitus" are to be construed as generally defined in the field, that is to say by a relative insulin deficiency and impaired glucose tolerance (IGT) which develop over time, unlike the absolute deficiency found in patients with type 1 diabetes mellitus. Type 2 diabetes mellitus is typically described as part of a dysmetabolic syndrome (syndrome X) that includes insulin resistance, hyperinsulinemia, obesity, hypertension, and dyslipidemia. Current knowledge suggests that the development of glucose intolerance or diabetes is initiated by insulin resistance and worsened by the compensatory hyperinsulinemia.

In the context of the invention, the term "gestational diabetes mellitus" is to be construed as generally defined in the field, that is to say as diabetes diagnosed in the second or third trimester of pregnancy that is not clearly overt diabetes, that is to say one of the type 1 or 2 diabetes mellitus as defined above.

In the context of the invention, the terms "other specific types of diabetes mellitus" refer to specific types of diabetes which do not fall into the previous categories, which include monogenic diabetes syndromes, diseases of the exocrine pancreas, and drug- or chemical induced diabetes.

In an embodiment, the compound of formula (I), one of its pharmaceutically acceptable salts, or a composition comprising thereof, is for use in the prevention or treatment of type 1 diabetes mellitus.

In another embodiment, the compound of formula (I), one of its pharmaceutically acceptable salts, or a composition comprising thereof, is for use in the prevention or treatment of pre-diabetes, in particular pre-diabetes with impaired fasting glucose and pre-diabetes with impaired glucose tolerance, type 2 diabetes mellitus, gestational diabetes mellitus, or other specific types of diabetes mellitus.

Preferably the subject is a mammal. Yet preferably the subject is a human. Advantageously, the subject is a human presenting with insulin resistance.

In the context of the invention, the terms "insulin resistance" should be construed as generally understood in the field, that is to say as a pathological condition in which cells fail to respond normally to the hormone insulin. A fasting serum insulin level greater than 25 mIU/L or 174 pmol/L is considered insulin resistance.

Preferably the compound of formula (I), one of its pharmaceutically acceptable salts or the composition comprising thereof, is administered through the parenteral route, preferably via intravenous, intramuscular, subcutaneous or intradermal administration. Yet preferably the compound of formula (I), one of its pharmaceutically acceptable salts or the composition comprising thereof, is administered through intravenous or subcutaneous administration, advantageously subcutaneous administration.

Preferably, the compound of formula (I), one of its pharmaceutically acceptable salts or the composition comprising thereof, is administered by injection or infusion, advantageously infusion.

As herein defined, the term "injection" refers to the continuous administration of liquid or medication in a subject, via intravenous or subcutaneous application, lasting less than 15 minutes. Infusion typically involves the administration of said fluid or medication through a needle or a catheter.

As herein defined, the term "infusion" refers to the continuous administration of liquid or medication in a subject, via intravenous or subcutaneous application, lasting at least 15 minutes. Infusion typically involves the administration of said fluid or medication through a needle, a catheter or an infusion pump. In the context of the invention, the term infusion encompasses continuous infusion, intermittent infusion and subject-controlled infusion. Continuous infusion typically comprises small pulses of infusion performed at a predetermined regular rate, with the rate of these pulses depending on the programmed infusion speed. Intermittent infusion typically comprises alternating pulses of high and low programmable infusion rates. Patient-controlled is a type of infusion where the rate is controlled by the patient, usually by a pressure pad or button.

Preferably, the compound of formula (I), one of its pharmaceutically acceptable salts or the composition comprising thereof, is administered by subcutaneous infusion. Yet preferably, the infusion, in particular the subcutaneous infusion, is a continuous infusion.

To this end, the composition according to embodiments of the disclosure may be formulated so as to facilitate the administration. Preferably, the composition according to embodiments of the disclosure is formulated as a liquid composition, such as for instance an aqueous suspension, isotonic saline solution or sterile injectable solution. Said compositions may optionally comprise pharmacologically-compatible dispersion agents and/or wetting agents.

Preferably, the at least one of the compounds of formula (I), one of its pharmaceutically acceptable salts or the composition comprising thereof, is administered in an effective amount.

The amount of a compound of general formula (I) or one of its pharmaceutically acceptable salts which is administered can be adjusted in order to obtain the desired therapeutic response. In the context of the invention, the desired therapeutic response can be considered as enhancing glucose-induced insulin secretion, and/or improving glucose homeostasis in a subject.

The effective therapeutic amount of a compound typically varies as a function of numerous parameters such as, for example, the administration route chosen, weight, age, sex, type of disease, sensitivity of the individual to be treated. Consequently the optimum amount for a specific subject can be established by the person skilled in the art as a function of parameters considered to be relevant.

Preferably the effective therapeutic amount is inferior to 240 mg/kg per 24 h for a human adult.

Advantageously, the effective amount is comprised between 0.01 and 100 mg/kg, preferably between 0.05 and 50 mg/kg, yet preferably between 0.1 and 10 mg/kg, per 24 h for a human adult.

In an embodiment, the effective amount is comprised between 0.01 and 25 mg/kg, preferably between 0.01 and 15 mg/kg, yet preferably between 0.01 and 5 mg/kg, per 24 h for a human adult.

In another embodiment, the effective amount is comprised between 10 and 100 mg/kg, preferably between 10 and 50 mg/kg, yet preferably between 10 and 25 mg/kg, per 24 h for a human adult.

Embodiments of the disclosed subject matter will be better understood in reference to the figure and the examples which follow.

Figure 1B:
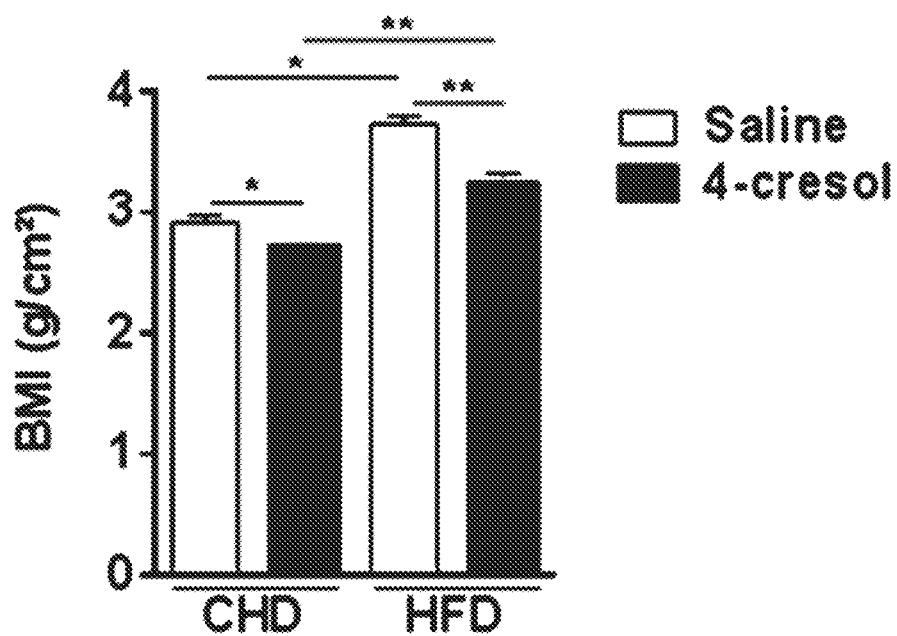
Figure 1C:
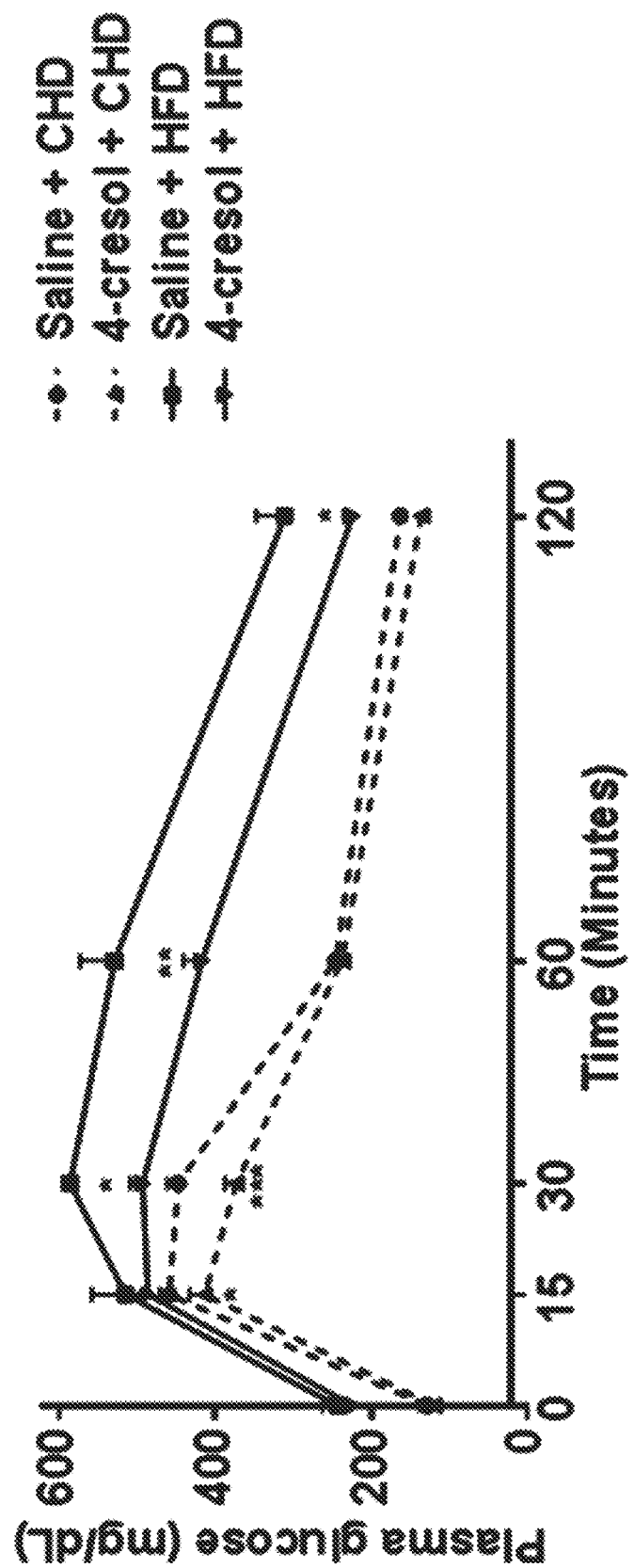
Figure 1D:
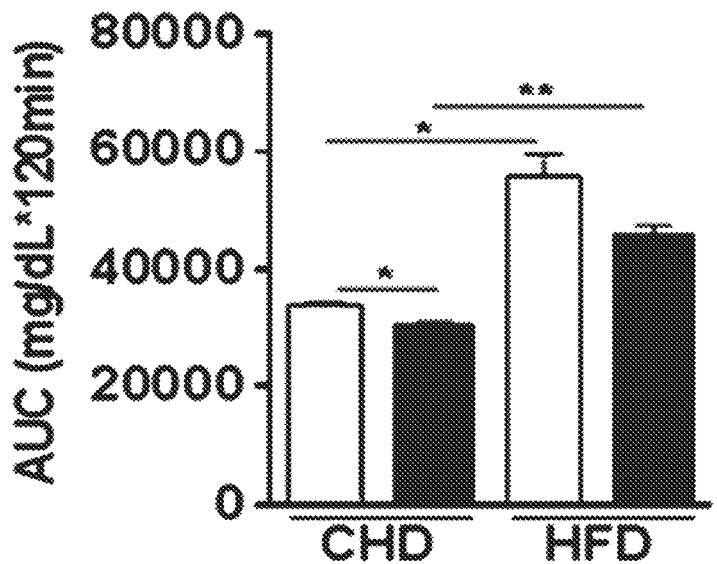
Figure 1E:
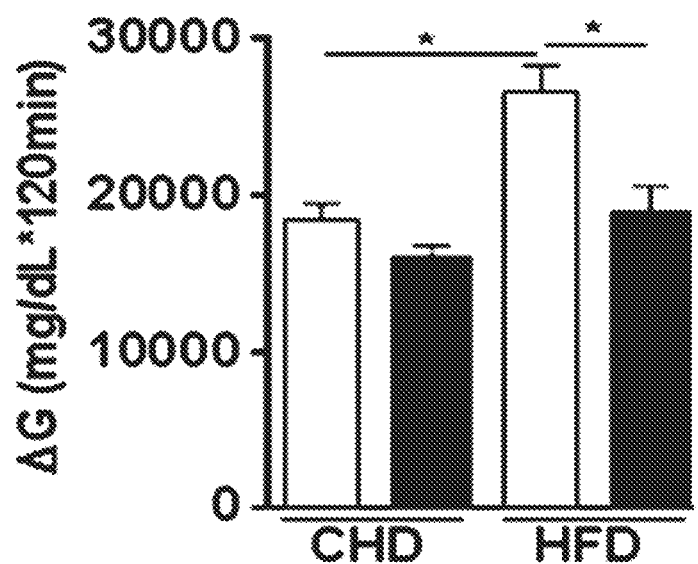
Figure 1F:
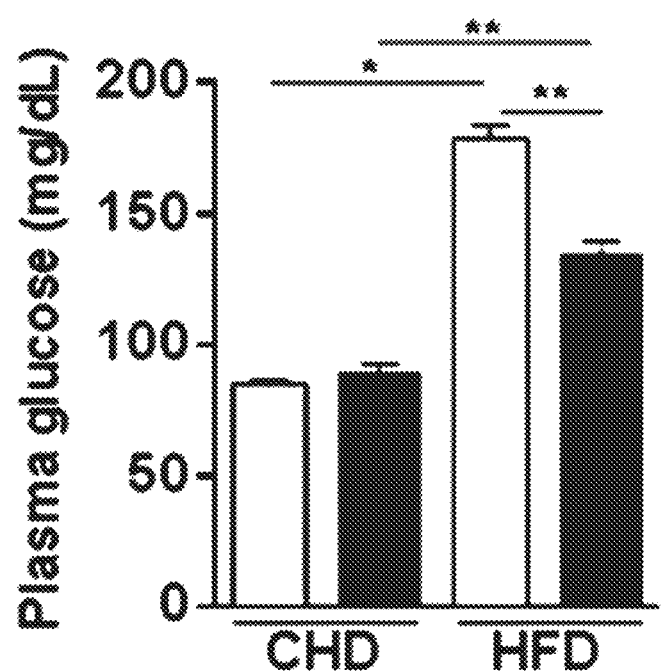
Figure 1G:
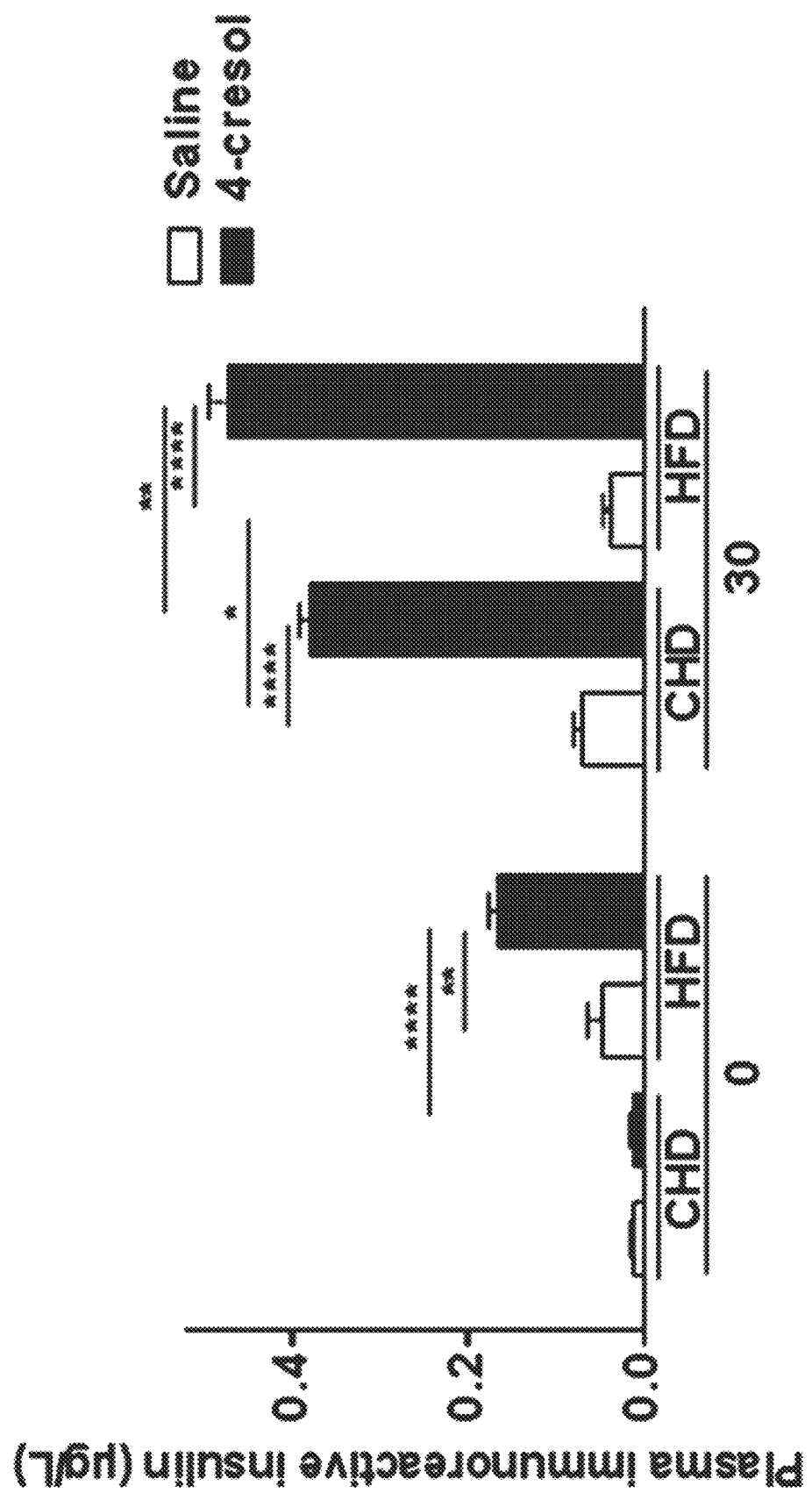
Figure 1H:
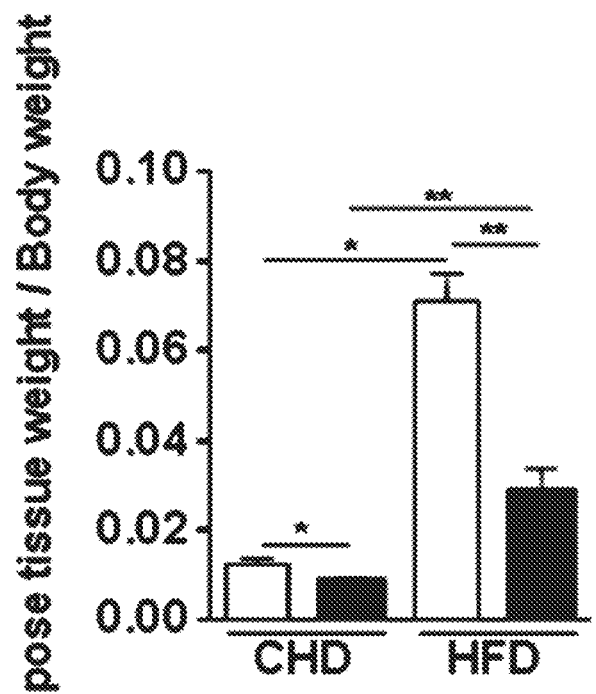
Figure 1I:
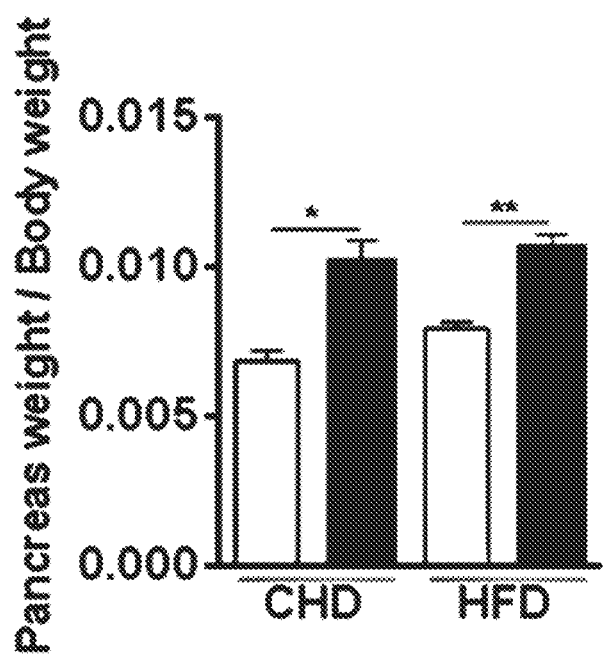
Figure 1J:
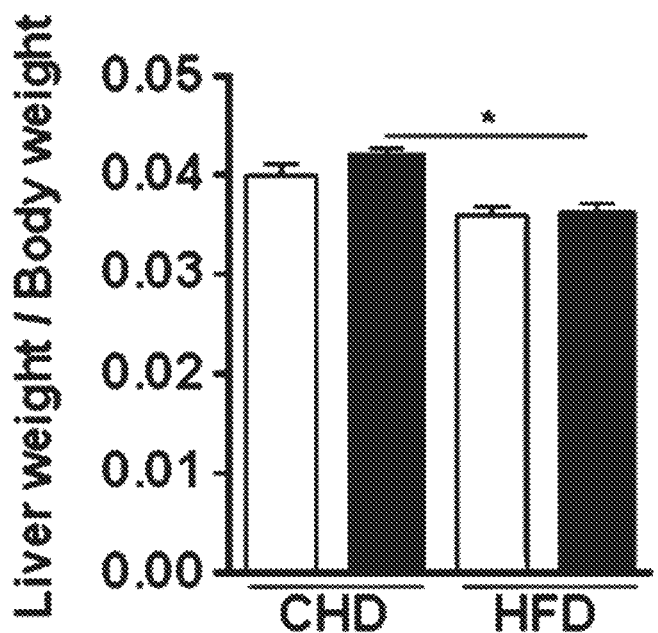
Figure 1K:
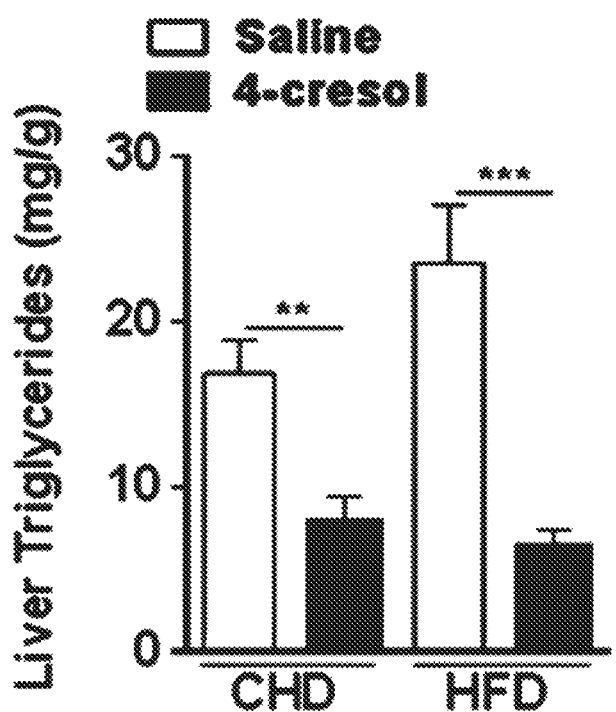

FIGS. 1A-1K show the impact of chronic administration of 4-cresol on body growth and glucose homeostasis. The effects of 6-week 4-cresol treatment in vivo in mice fed control chow or high fat diet (HFD) were tested on body weight (FIG. 1A), body mass index (BMI) (FIG. 1B), glucose homeostasis (FIGS. 1C-1F), glucose-stimulated insulin secretion (FIG. 1G), organ weight (FIGS. 1H-1J) and liver triglycerides (FIG. 1K). BMI was calculated as body weight divided by the squared of anal-nasal length. AUC was calculated as the sum of plasma glucose values during the IPGTT. ΔG is the AUC over the baseline value integrated over the 120 minutes of the test. All measures are from 6 mice per group. Data were analyzed using the unpaired Mann-Whitney test. Results are means±SEM. *$P<0.05$; $P<0.01$; *$P<0.001$; ****$P<0.0001$, significantly different to relevant controls.

Figure 2A:
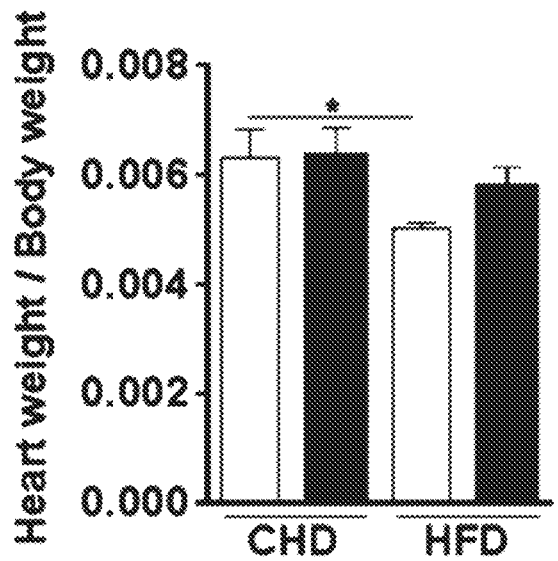
FIGS. 2A-2B show the effects of chronic treatment of C57BL6/J mice in vivo with 4-cresol on heart weight (FIG. 2A) and kidney weight (FIG. 2B).
Figure 2B:
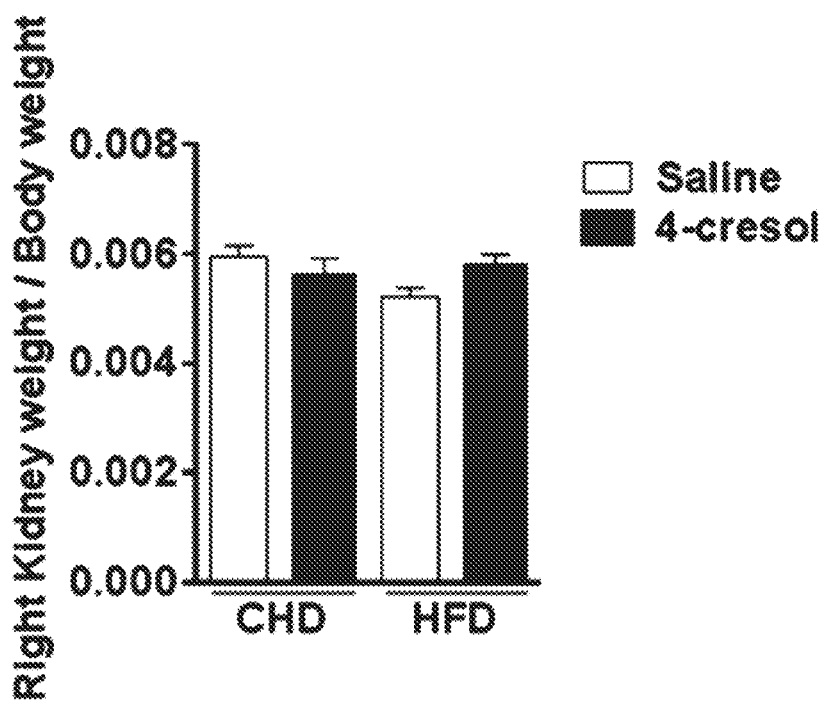
Figure 3A:
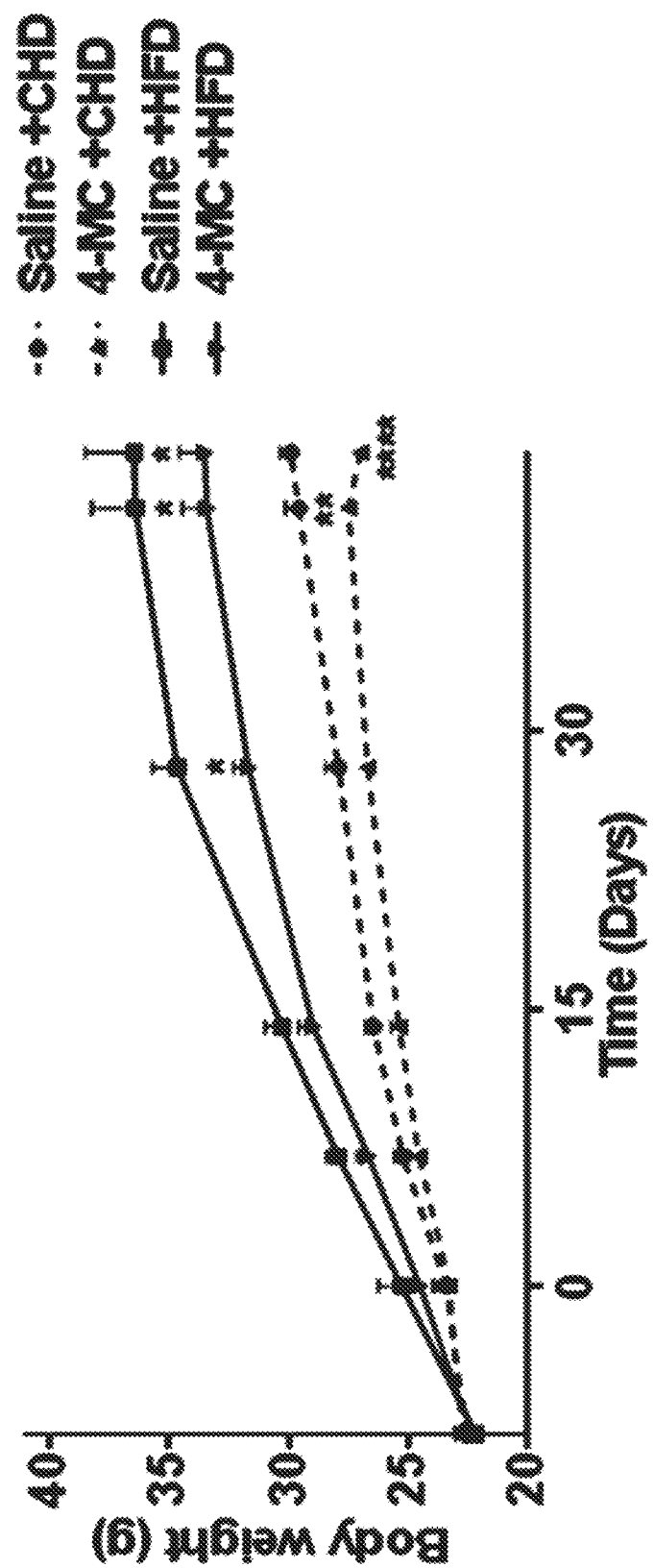
FIGS. 3A-3I show the impact of chronic administration of 4-methylcatechol on body growth and glucose homeostasis.
Figure 3B:
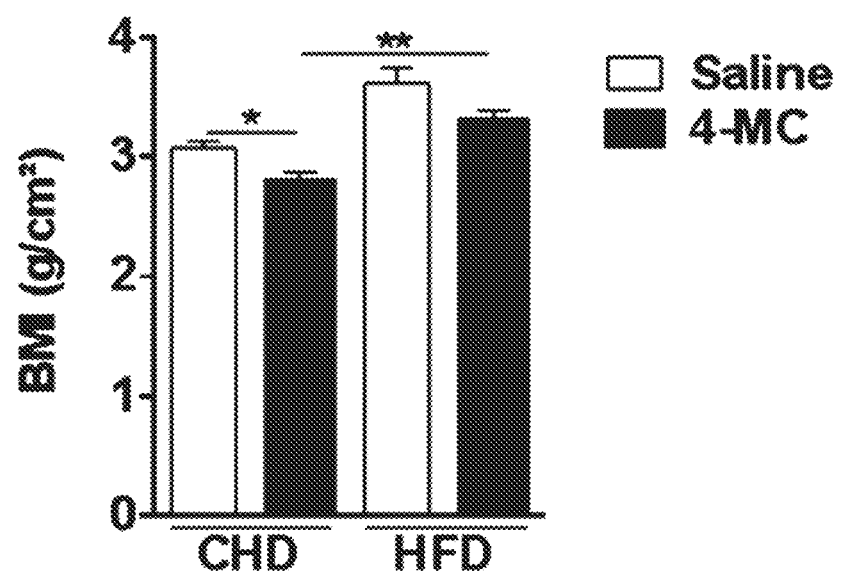
Figure 3C:
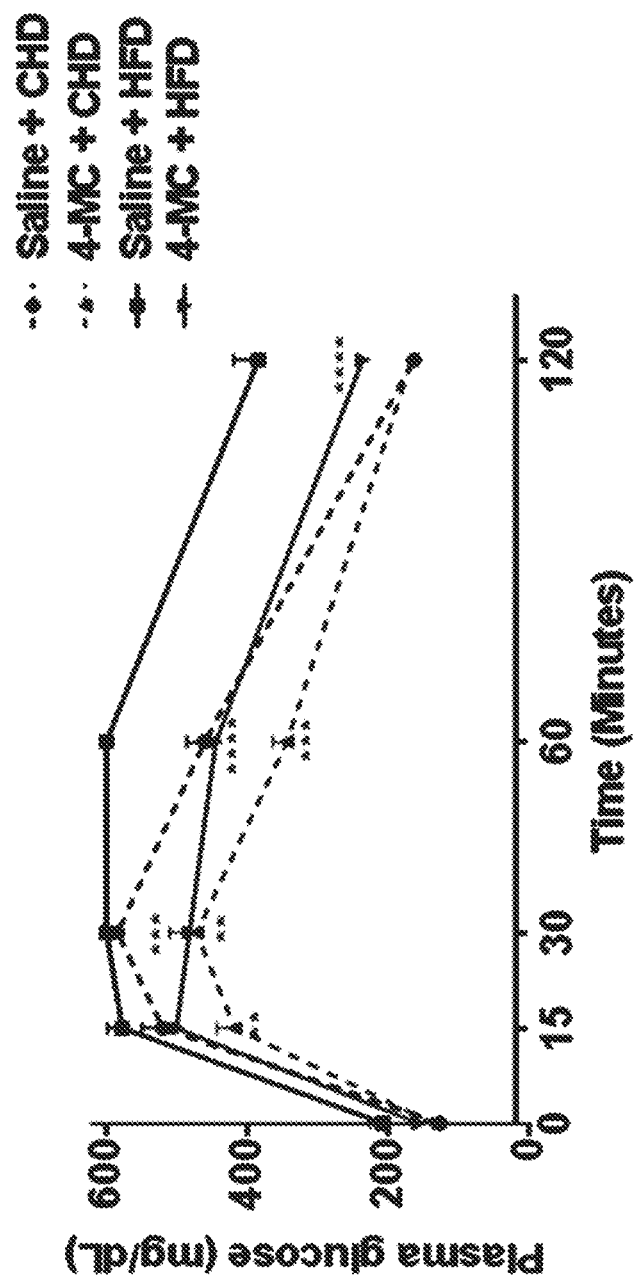
Figure 3D:
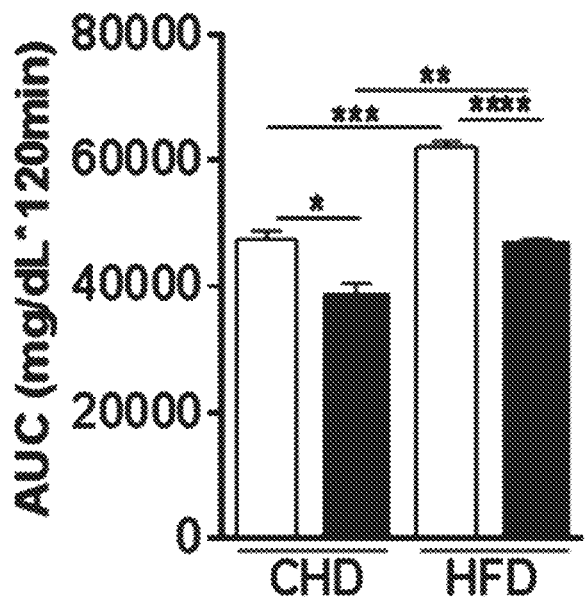
Figure 3E:
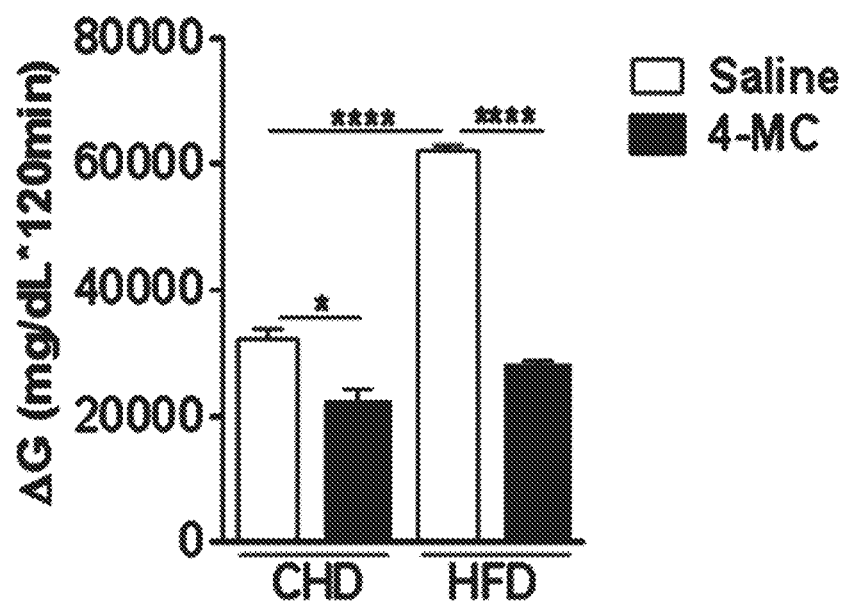
Figure 3F:
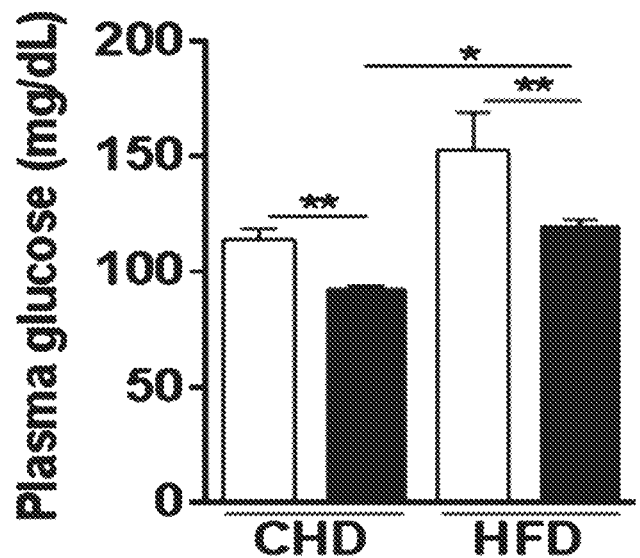
Figure 3G:
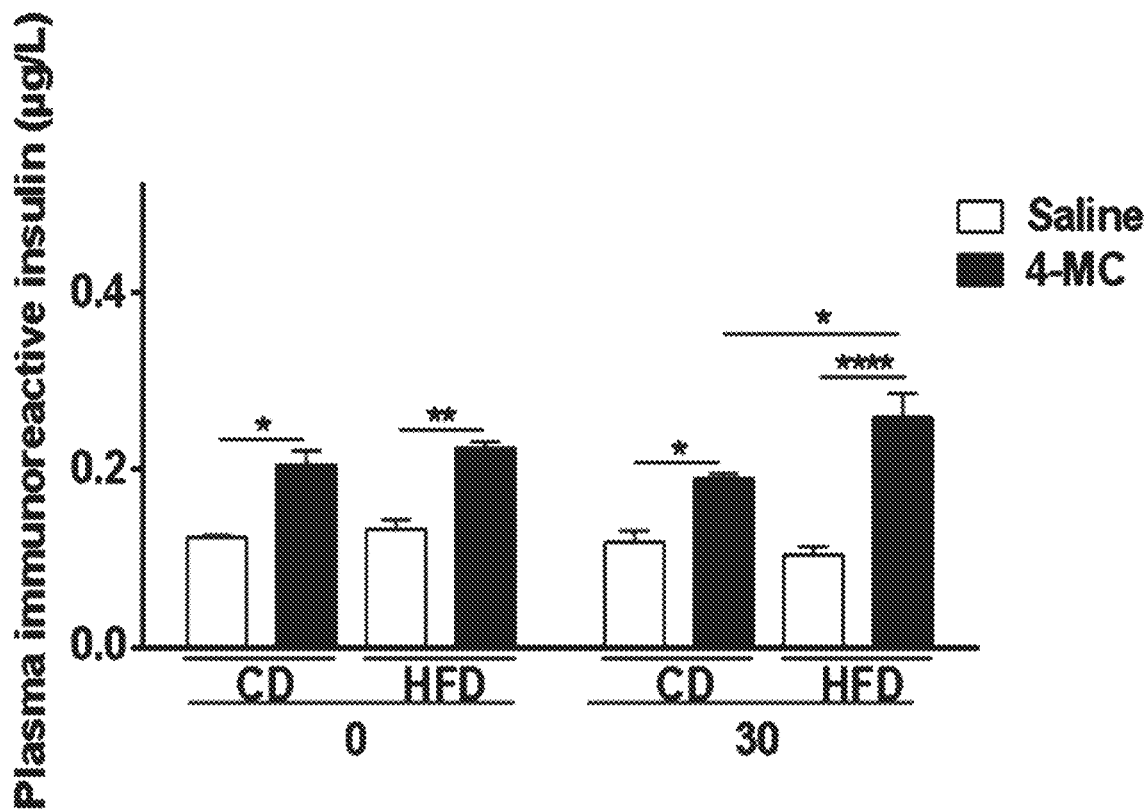
Figure 3H:
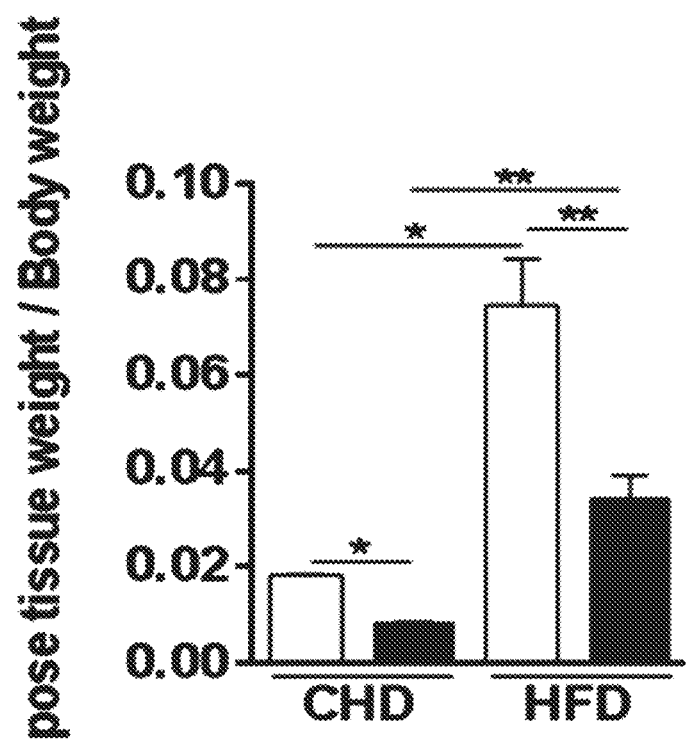
Figure 3I:
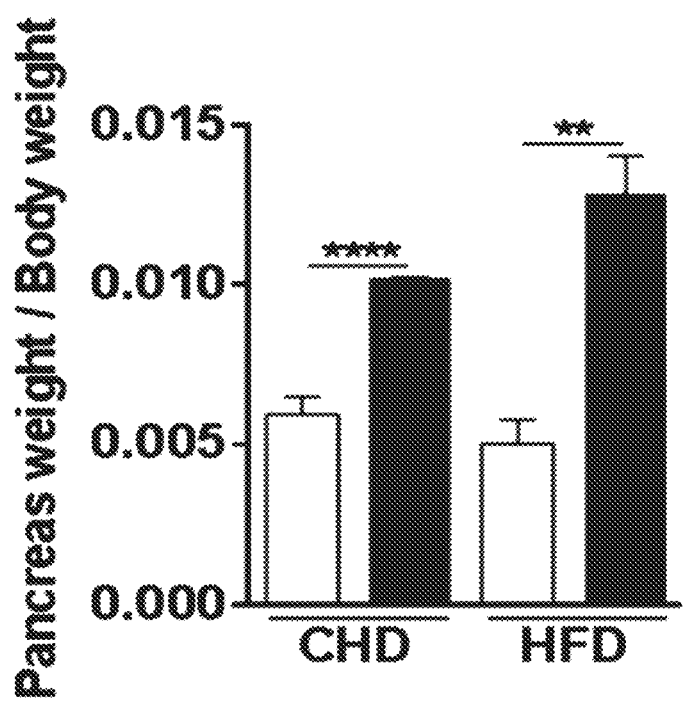

FIGS. 2A-2B show the effects of chronic treatment of C57BL6/J mice in vivo with 4-cresol on heart weight (FIG. 2A) and kidney weight (FIG. 2B). Mice were fed either control chow diet (CHD) or high fat diet (HFD). Data were analyzed using the unpaired Mann-Whitney test. Results are means±SEM. *$P<0.05$ significantly different to relevant controls.

FIGS. 3A-3I show the impact of chronic administration of 4-methylcatechol on body growth and glucose homeostasis. The effects of 6-week 4-methylcatechol (4-MC) treatment in vivo in mice fed control chow or high fat diet (HFD) were tested on body weight (FIG. 3A), body mass index (BMI) (FIG. 3B), glucose homeostasis (FIGS. 3C-3F), glucose-stimulated insulin secretion (FIG. 3G), organ weight (FIG. 3H-3J) and liver triglycerides (FIG. 3K). BMI was calculated as body weight divided by the squared of anal-nasal length. AUC was calculated as the sum of plasma glucose values during the IPGTT. ΔG is the AUC over the baseline value integrated over the 120 minutes of the test. All measures are from 6 mice per group. Data were analyzed using the unpaired Mann-Whitney test. Results are means±SEM. *$P<0.05$; $P<0.01$; *$P<0.001$; ****$P<0.0001$, significantly different to relevant controls.

Figure 4A:
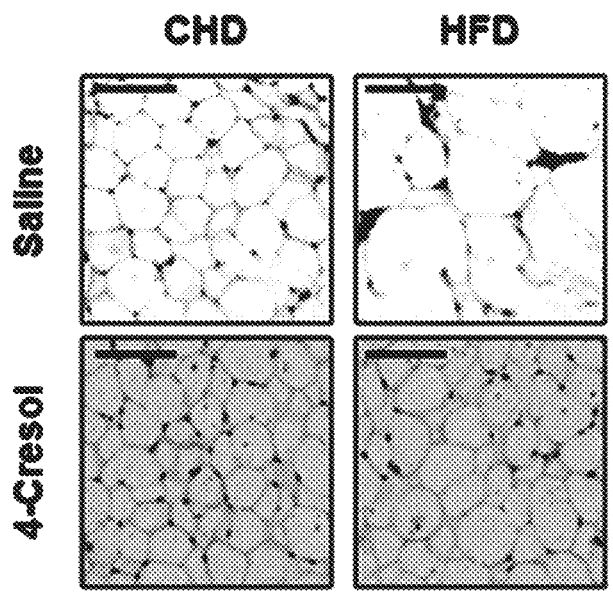
FIGS. 4A-4D show the effects of chronic treatment of mice by 4-cresol on structural changes in adipose tissue (FIGS. 4A, 4B) and liver (FIGS. 4C, 4D).
Figure 4B:
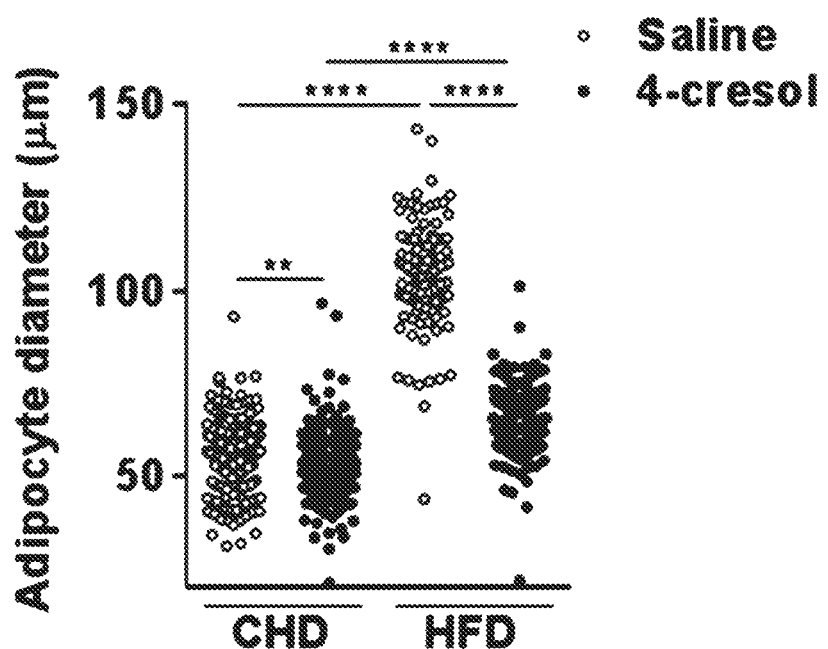
Figure 4C:
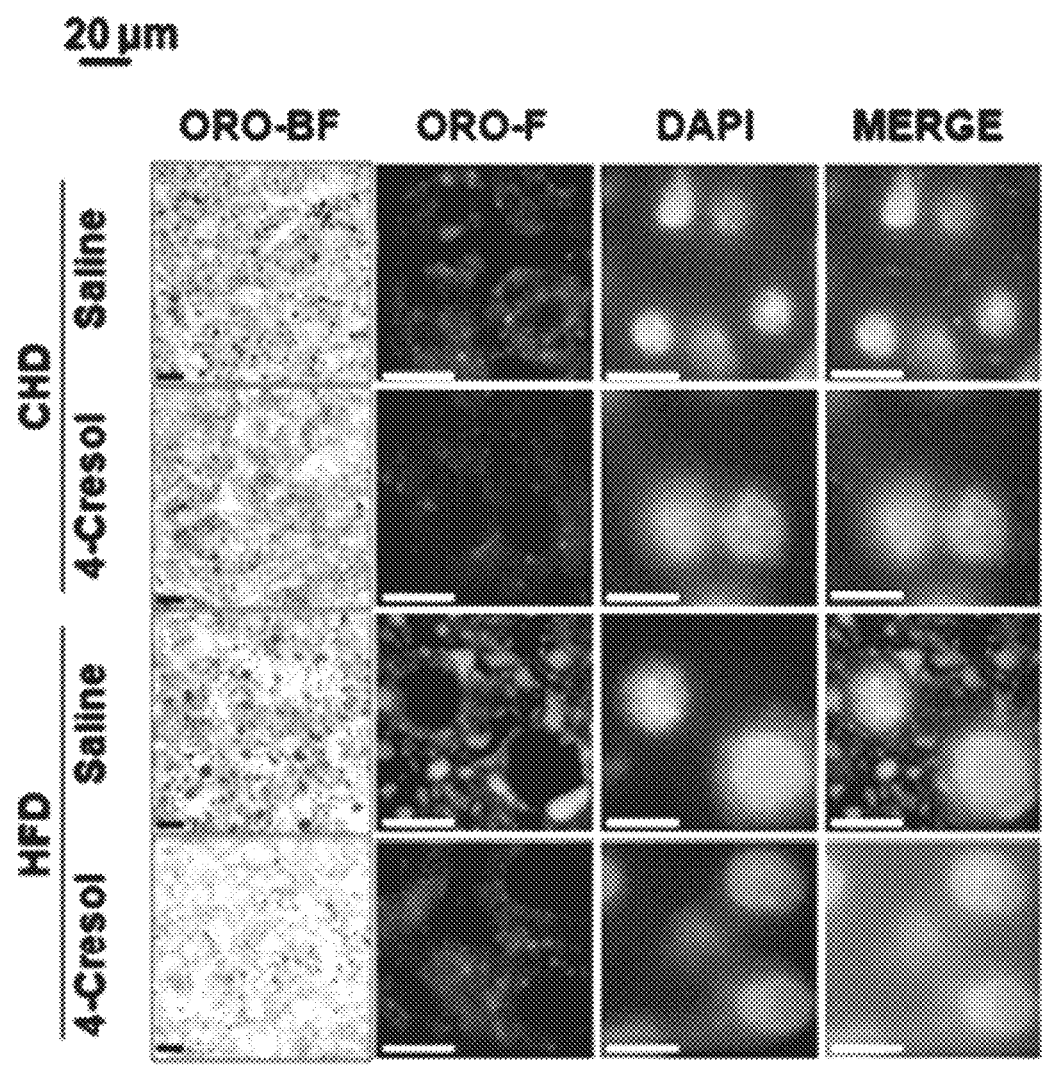
Figure 4D:
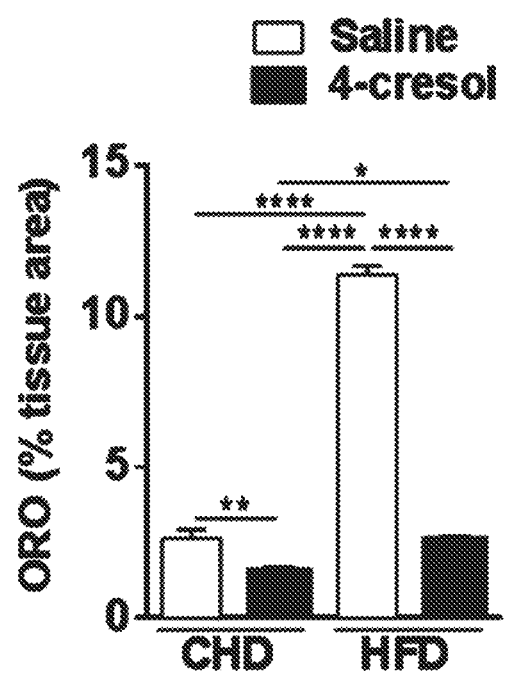
Figure 5A:
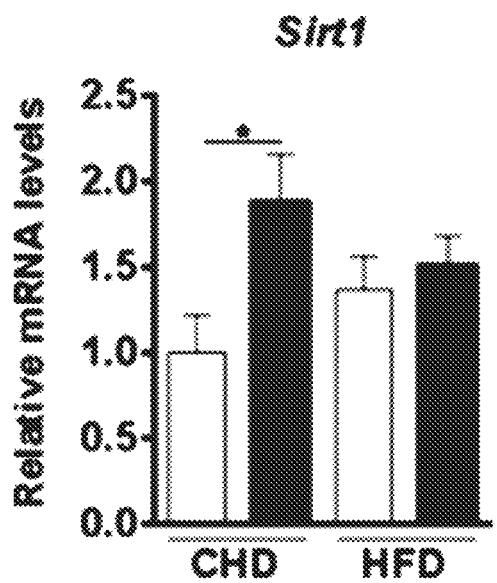
FIGS. 5A-5F show the effects of chronic treatment of mice by 4-cresol in vivo on gene expression in adipose tissue.
Figure 5B:
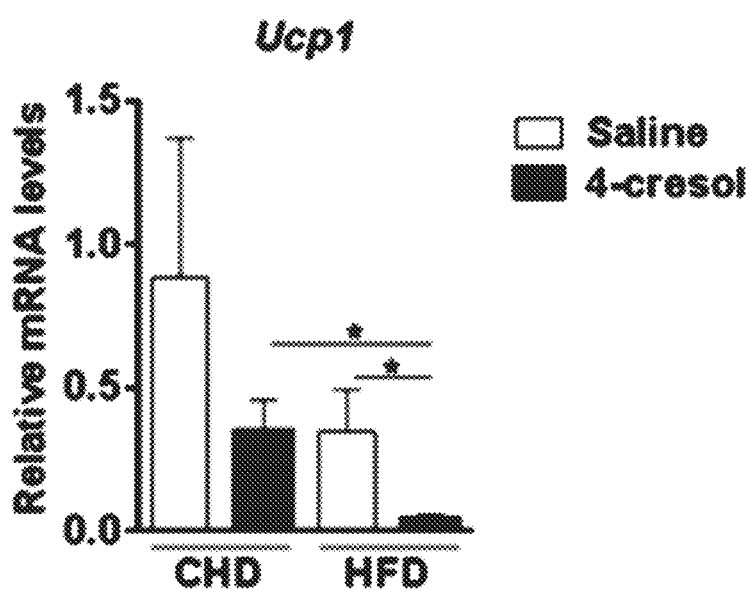
Figure 5C:
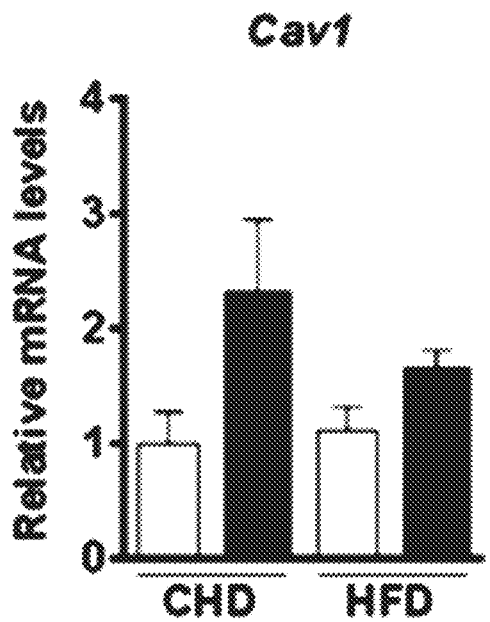
Figure 5D:
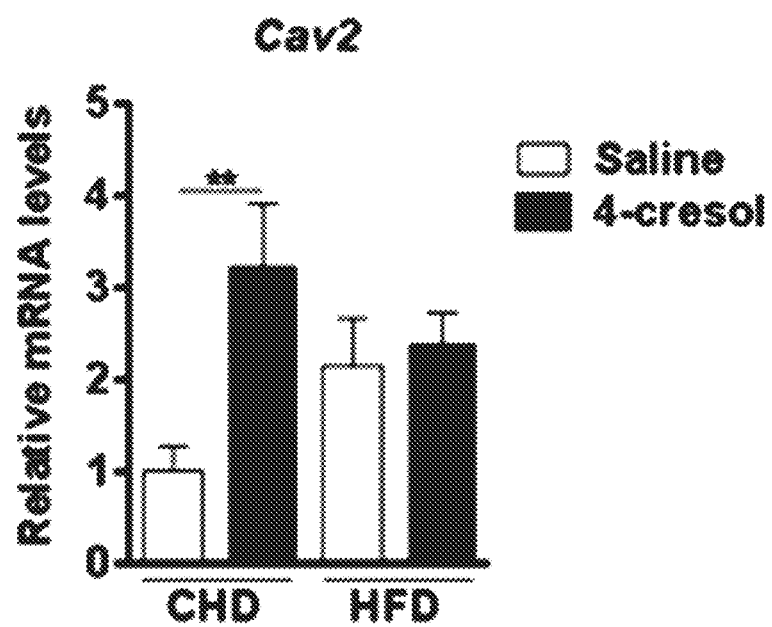
Figure 5E:
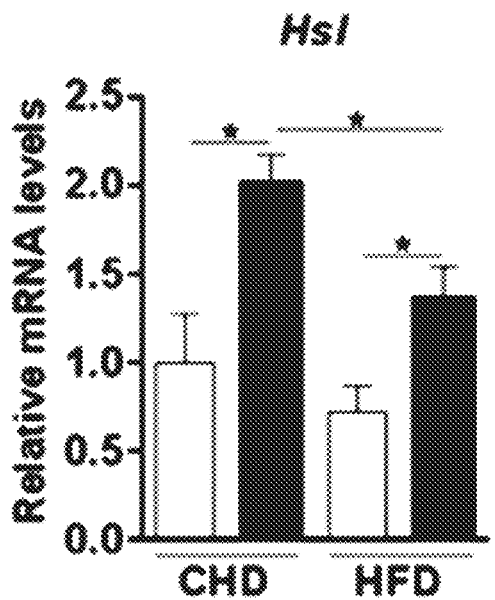
Figure 5F:
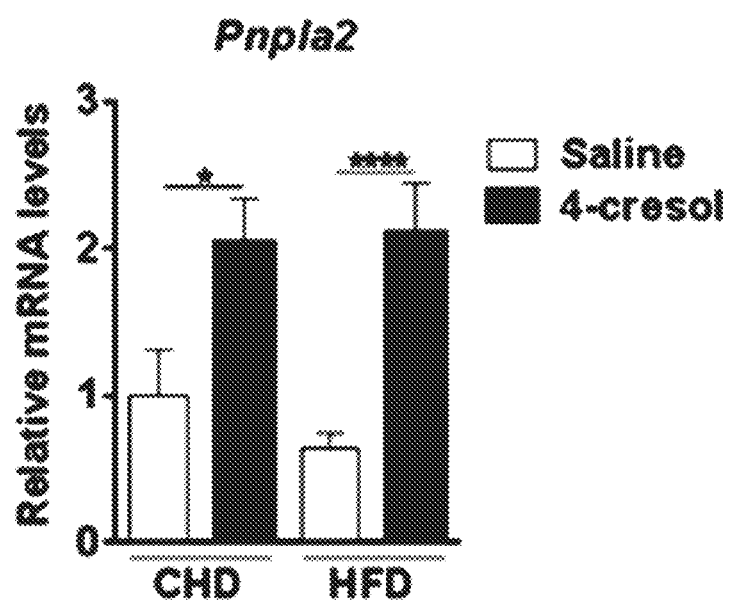

FIGS. 4A-4D show the effects of chronic treatment of mice by 4-cresol on structural changes in adipose tissue (FIGS. 4A,4B) and liver (FIGS. 4C,4D). Mice were fed normal chow diet (CHD) or high fat diet (HFD) and treated with chronic infusion of either 4-cresol or saline for 6-weeks. Adipose tissue sections were labeled either with Hematoxylin-Eosin (HE) (FIG. 4A) to determine adipocyte size (FIG. 4B). Liver sections were labeled with Oil Red 0 (ORO) (FIG. 4C) to determine neutral fat content (FIG. 4D). All measures are from 6 mice per group. A total of 2000 cells (8000 cells per group) were analyzed to determine adipocyte diameter. Data were analyzed using the unpaired Mann-Whitney test. Results are means±SEM. *$P<0.05$; $P<0.01$; *$P<0.001$, significantly different to relevant controls. ORO-BF, ORO bright field; ORO-F, ORO fluorescent.

FIGS. 5A-5F show the effects of chronic treatment of mice by 4-cresol in vivo on gene expression in adipose tissue. Transcript abundance of key genes regulating adipose tissue biology was tested by quantitative RT-PCR in retro-peritoneal fat pads of mice fed control chow diet (CHD) or high fat diet (HFD). Data were analyzed using the unpaired Mann-Whitney test. Results are means±SEM. *$P<0.05$; $P<0.01$; **$P<0.0001$ significantly different to relevant controls.

Figure 6A:
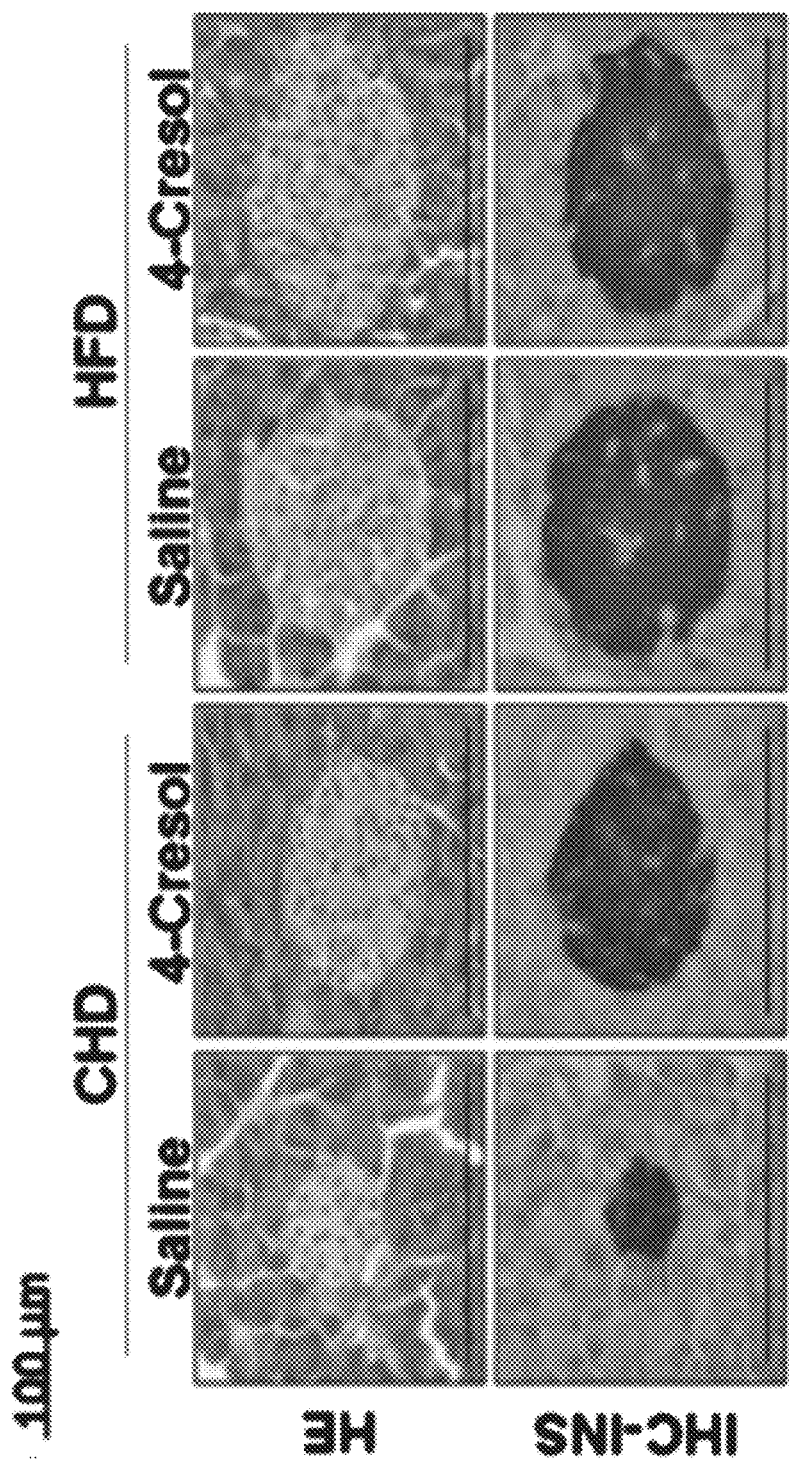
FIGS. 6A-6D show the effects of chronic treatment of mice bv 4-cresol on structural features of the pancreas.
Figure 6B:
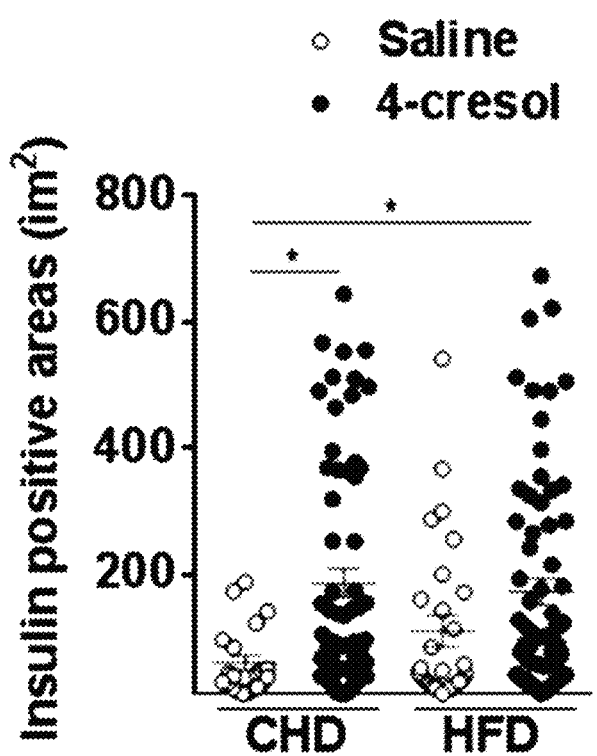
Figure 6C:
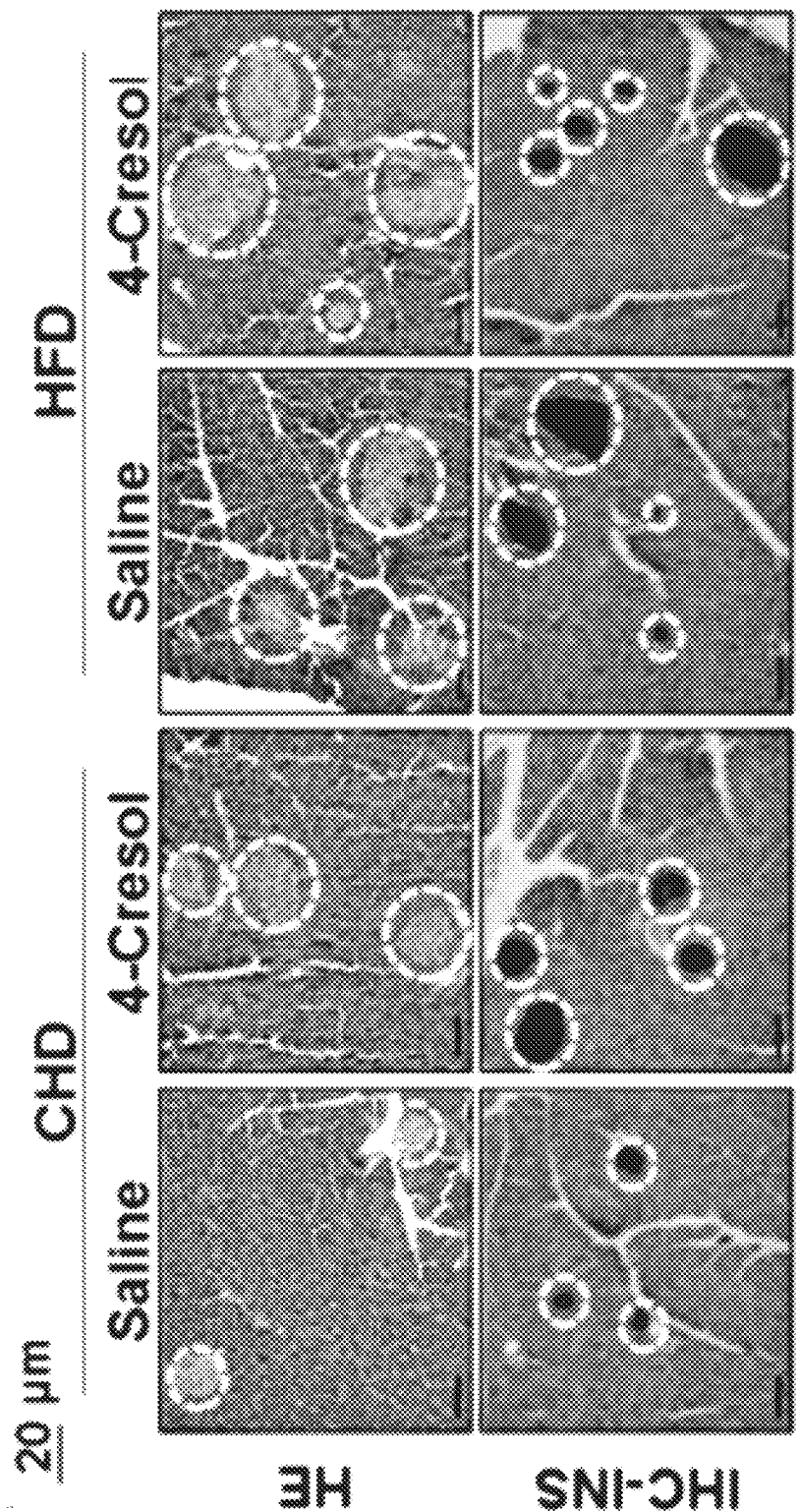
Figure 6D:
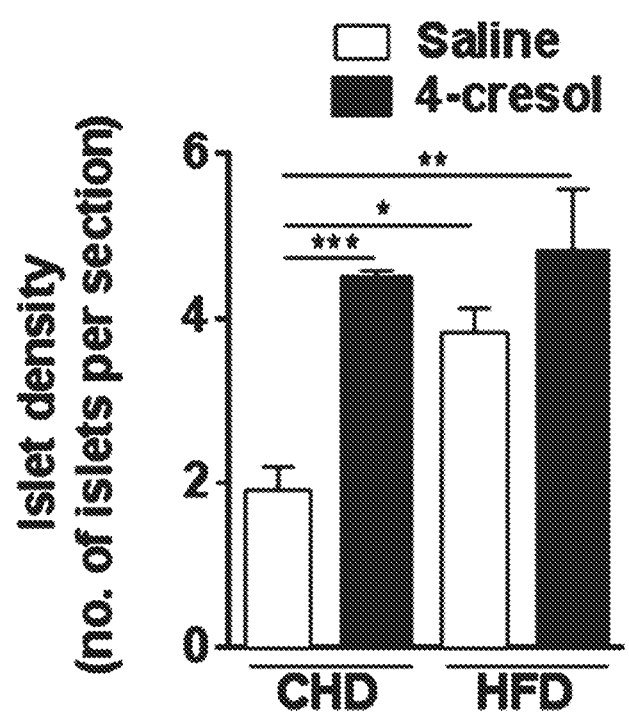

FIGS. 6A-6D show the effects of chronic treatment of mice by 4-cresol on structural features of the pancreas. Mice were fed normal chow diet (CHD) or high fat diet (HFD) and treated with chronic infusion of either 4-cresol or saline for 6-weeks. Pancreas sections were labeled either with Hematoxylin-Eosin (HE) and Immunohistochemistry (IHC) (FIG. 6A) to determine insulin positive area (FIG. 6B) and islet density (FIGS. 6C,6D). Results are means±SEM. *$P<0.05$; $P<0.01$; *$P<0.001$ significantly different to relevant controls.

Figure 7A:
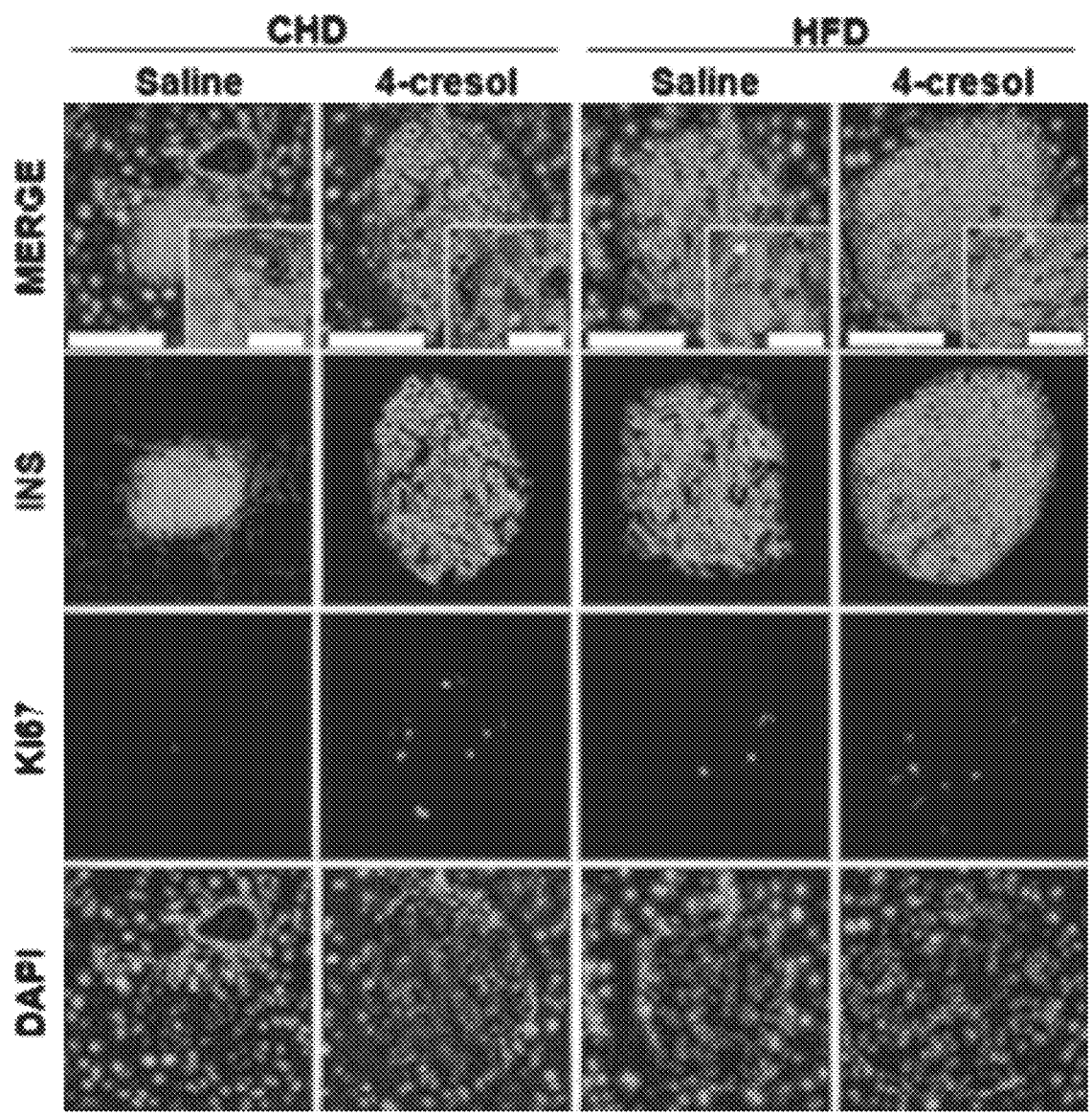
Figure 7E:
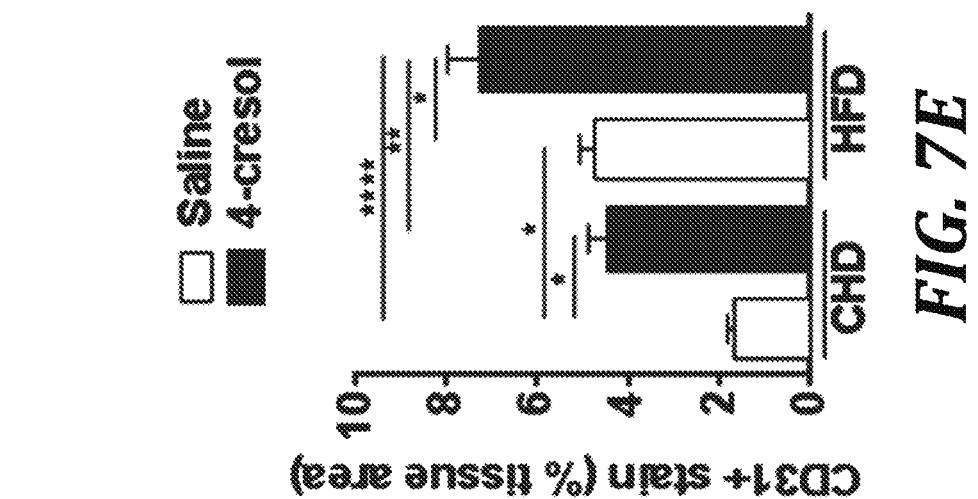
Figure 7D:
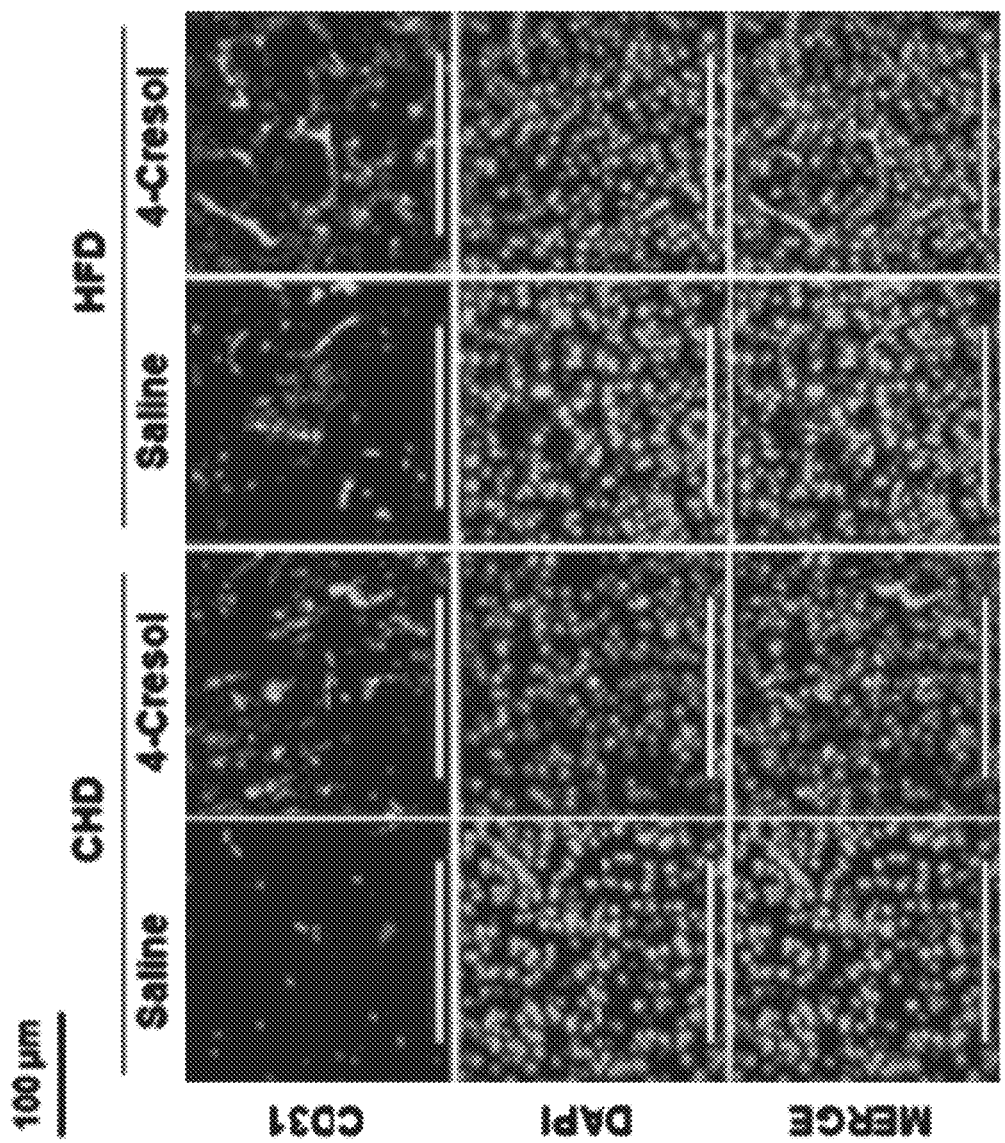

FIGS. 7A-7E show the effects of chronic treatment of mice by 4-cresol on pancreas cell proliferation and vascularization. Mice were fed normal chow diet (CHD) or high fat diet (HFD) and treated with chronic infusion of either 4-cresol or saline for 6-weeks. Pancreas sections were treated with KI67 and DAPI to stain proliferative nuclei (FIGS. 7A-7C) and CD31 and DAPI to stain and quantify endothelial cells (FIGS. 7D,7E). Results are means±SEM. *$P<0.05$; $P<0.01$; *$P<0.001$ significantly different to relevant controls.

Figure 8D:
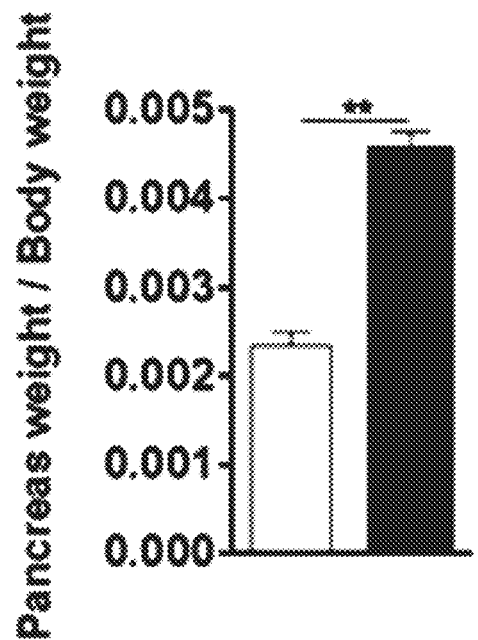
Figure 8E:
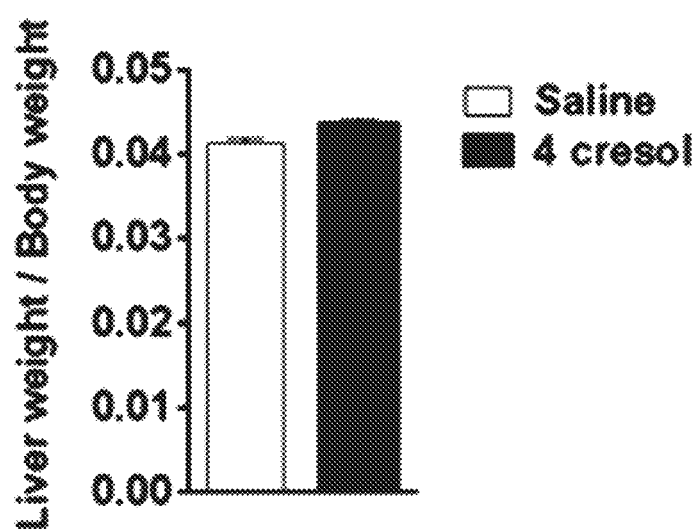

FIGS. 8A-8E show the effects of chronic administration of 4-cresol in vivo in Goto-Kakizaki (GK) rats on body weight and organ weight. The effects of 6-weeks 4-cresol treatment in vivo in GK rats were tested on body weight (FIG. 8A), body mass index (BMI) (FIG. 8B) and organ weight (FIG. 8C-8E). BMI was calculated as body weight divided by the squared of anal-nasal length. All measures are from 6 rats per group. Data were analyzed using the unpaired Mann-Whitney test. Results are means±SEM. *$P<0.05$; **$P<0.01$ significantly different to GK treated with saline.

Figure 9A:
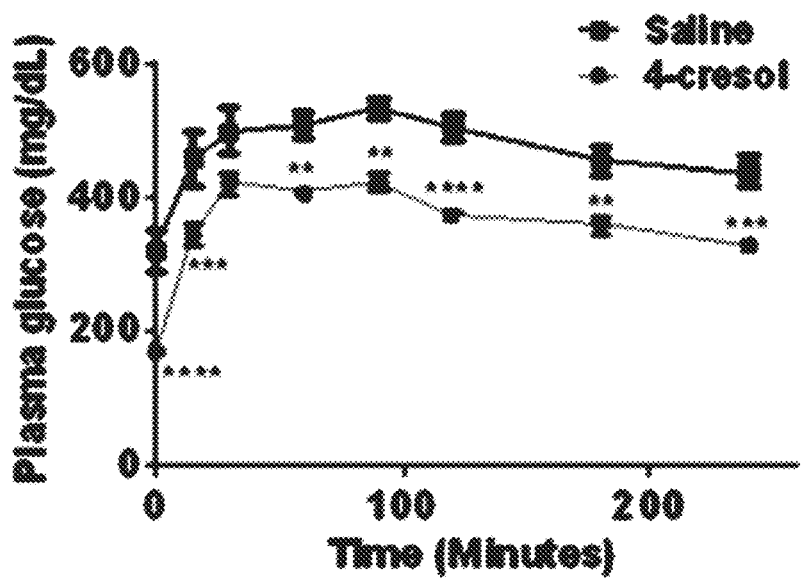
FIGS. 9A-9G show the impact of chronic administration of 4-cresol on diabetes related phenotypes in Goto-Kakizaki rats.
Figure 9B:
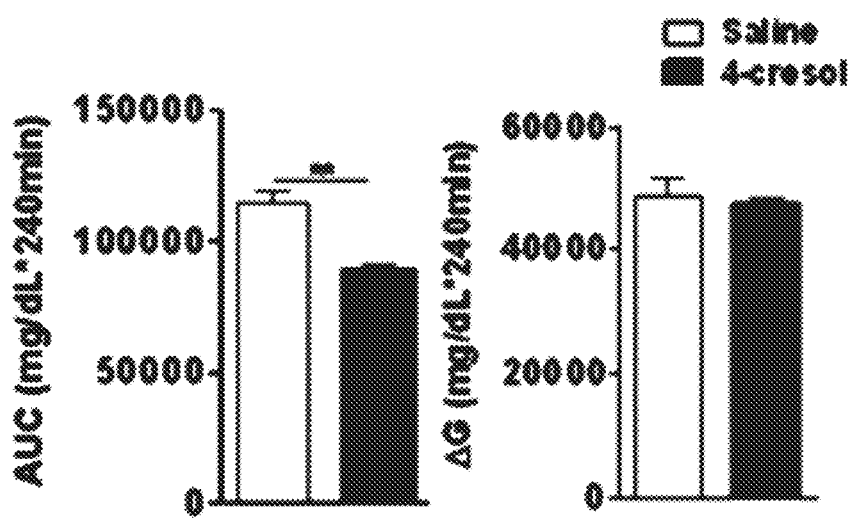
Figure 9C:
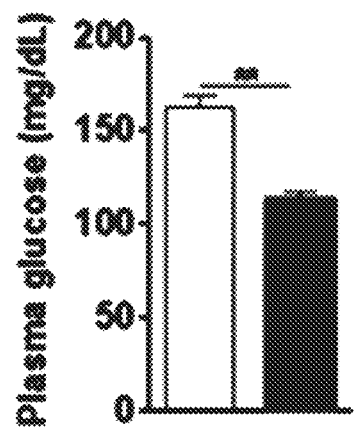
Figure 9D:
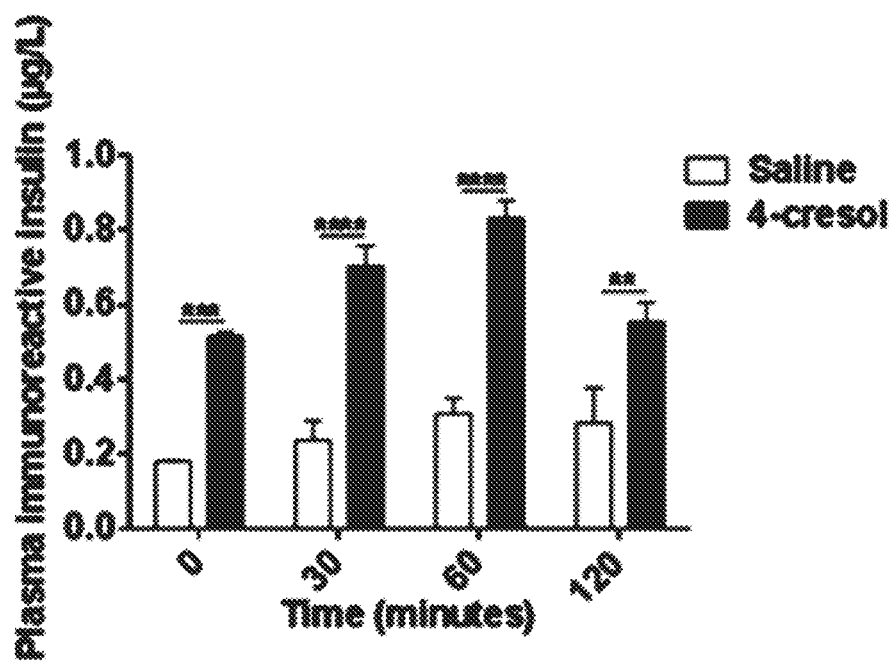
Figure 9E:
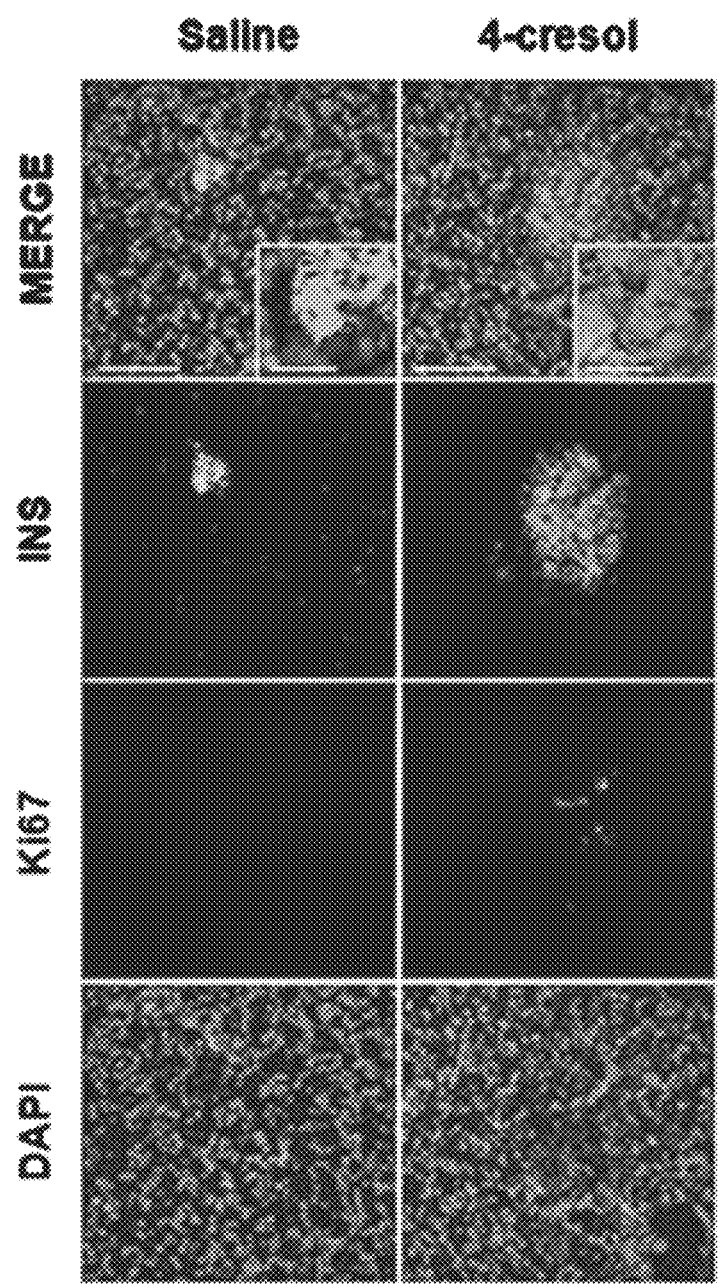
Figure 9F:
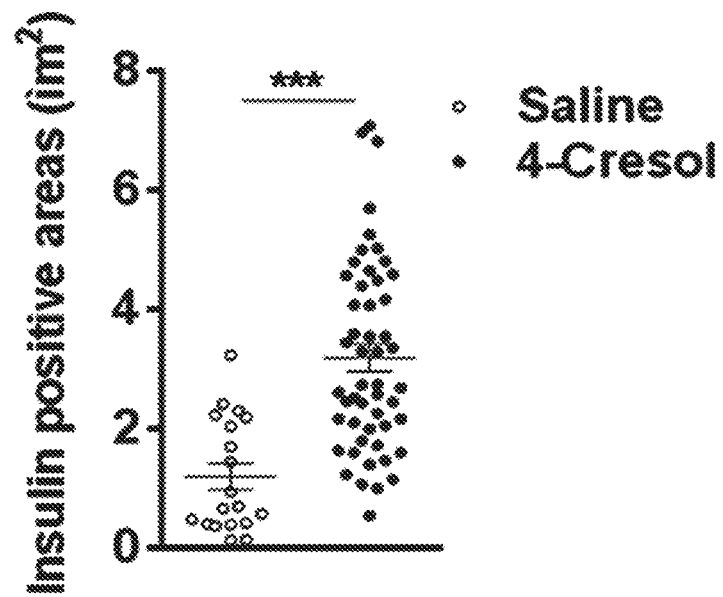
Figure 9G:
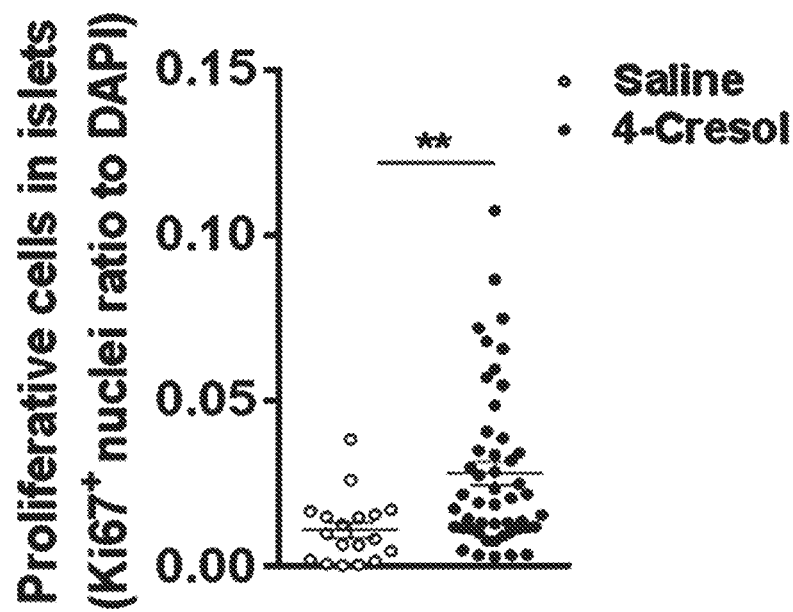

FIGS. 9A-9G show the impact of chronic administration of 4-cresol on diabetes related phenotypes in Goto-Kakizaki rats. Glucose homeostasis (FIGS. 9A-9C), glucose-stimulated insulin secretion (FIG. 9D) and pancreas histopathology (FIGS. 9E-9G) were determined in rats of the Goto-Kakizaki (GK) model of type 2 diabetes chronically treated with 4-cresol for 6-weeks. Pancreas sections were labeled either with Hematoxylin-Eosin and Immunohistochemistry to determine insulin positive area (FIG. 9F) and treated with Ki 67 and DAPI to stain and quantify proliferative nuclei (FIG. 9G). AUC was calculated as the sum of plasma glucose values during the IPGTT. ΔG is the AUC over the baseline value integrated over the first 240 minutes of the test. All measures are from 6 rats per group. Data were analyzed using the unpaired Mann-Whitney test. Results are means±SEM. $P<0.01$; *$P<0.001$; ****$P<0.0001$, significantly different to GK rats treated with saline.

Figures 10A, 10B, 10C:
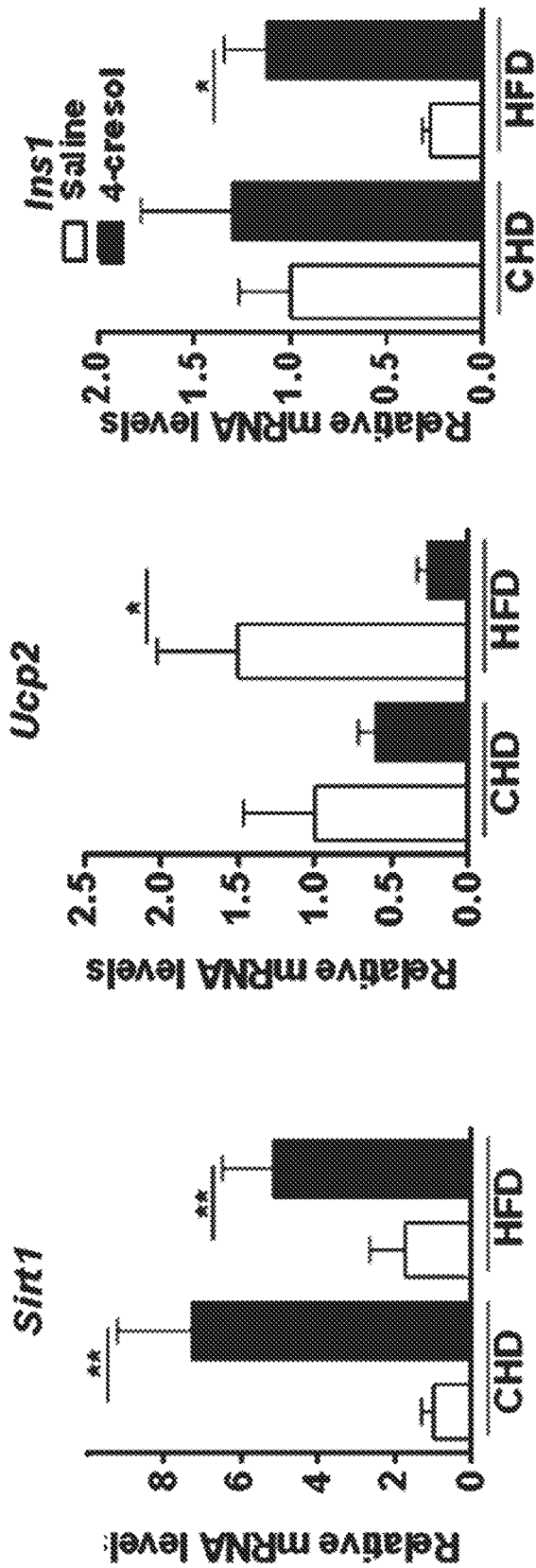
FIGS. 10A-10U show the effects of chronic administration of 4-cresol in fat fed mice and Goto-Kakizaki rats on pancreas gene expression.
Figure 10D:
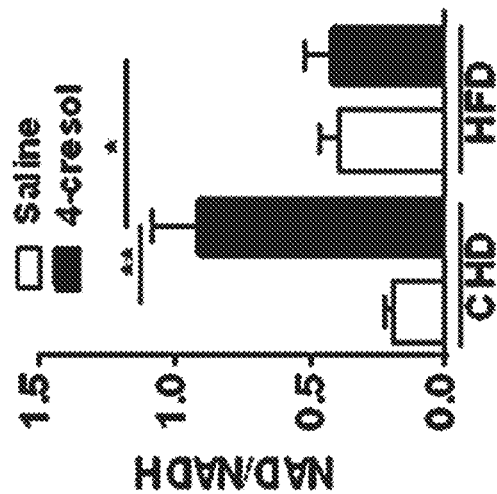
Figure 10E:
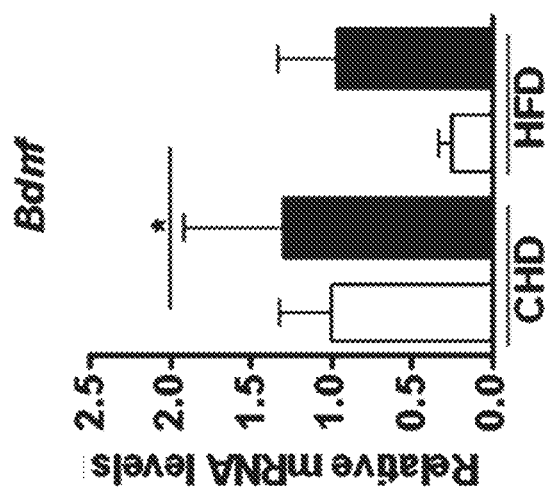
Figure 10F:
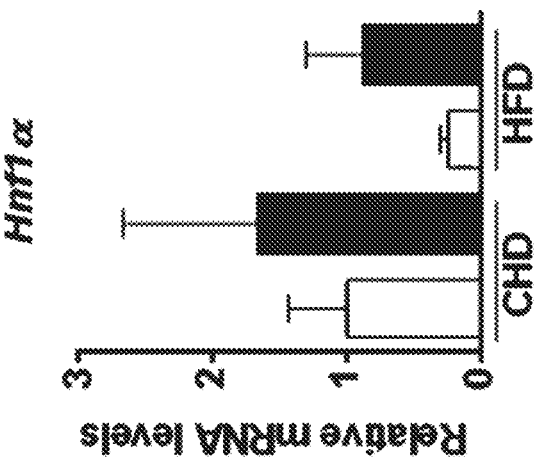
Figure 10G:
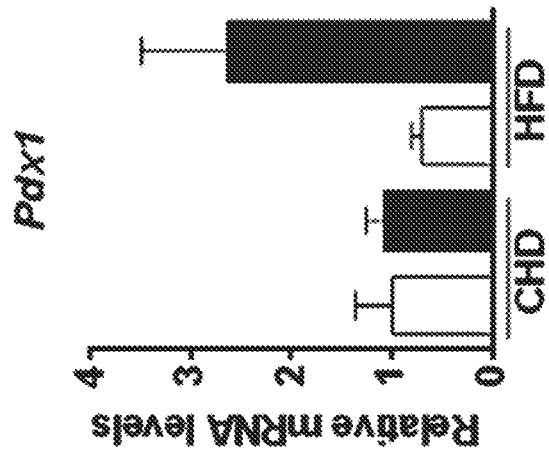
Figure 10H:
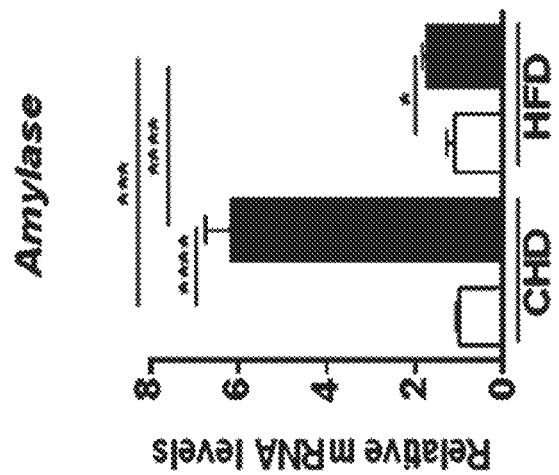
Figure 10I:
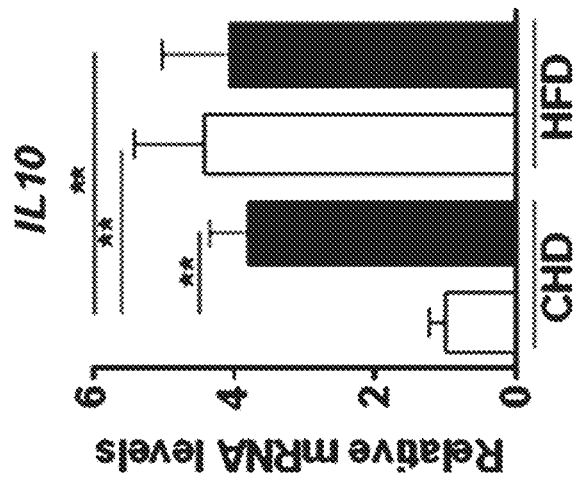
Figure 10L:
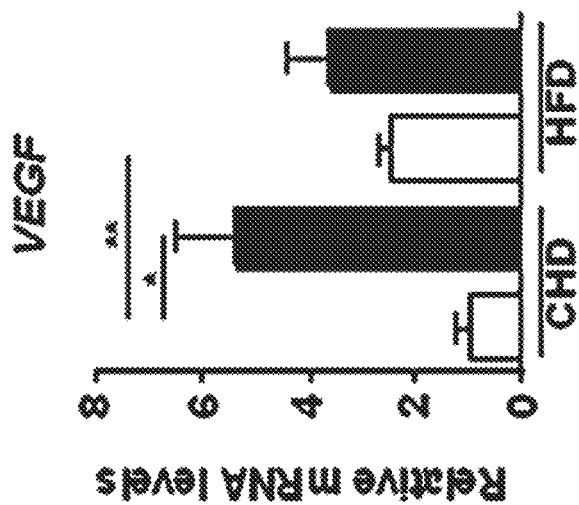
Figure 10K:
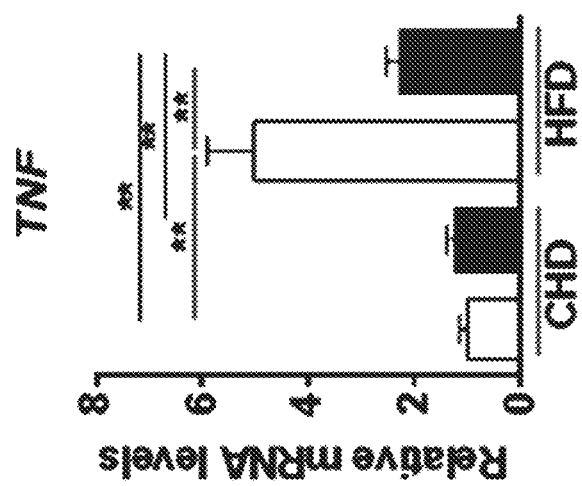
Figure 10J:
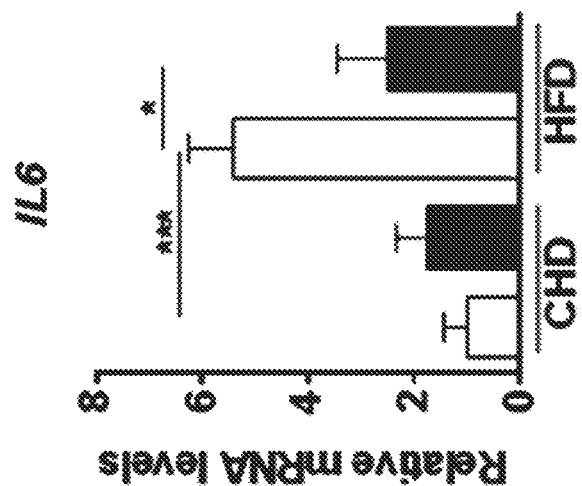
Figure 10M:
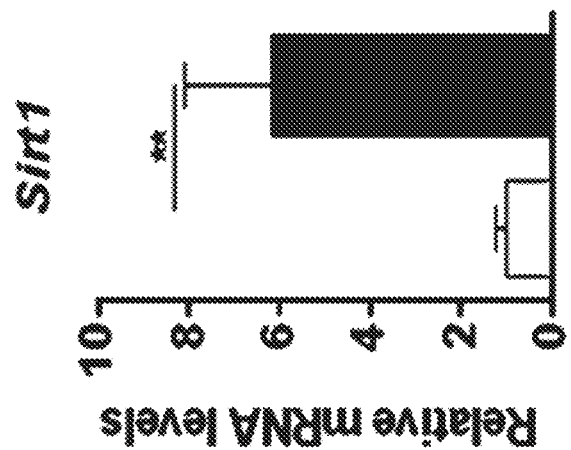
Figure 10N:
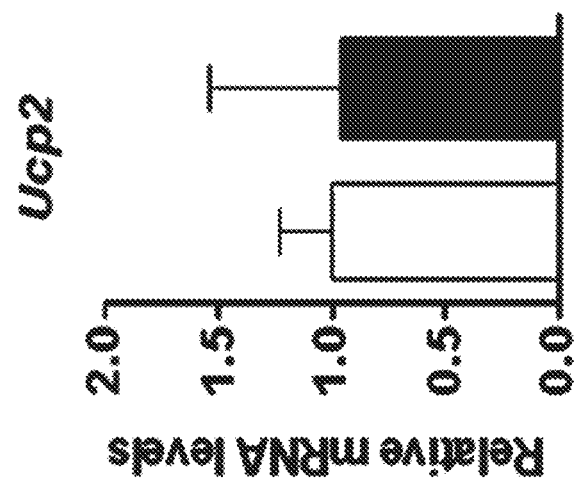
Figure 10P:
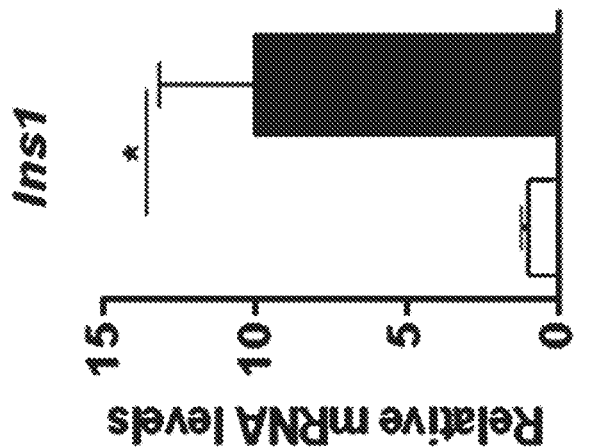
Figure 10U:
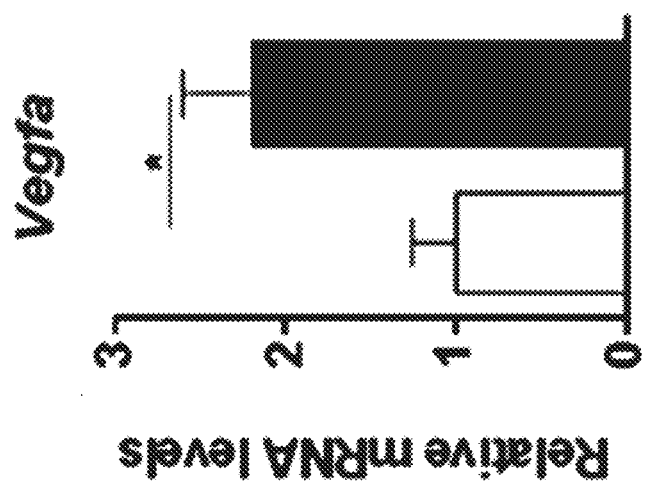
Figure 10T:
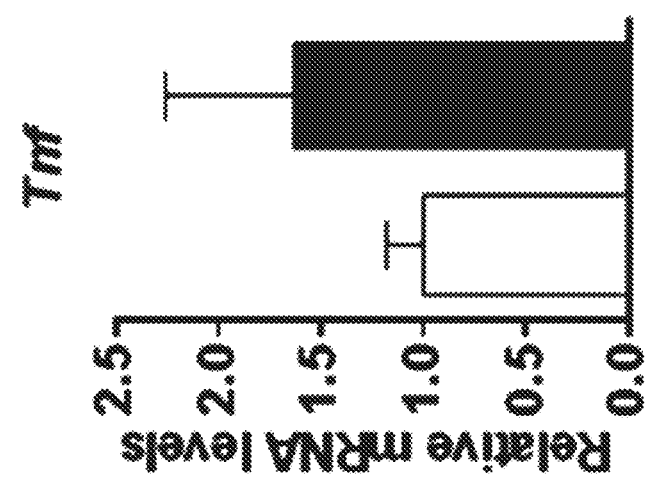

FIGS. 10A-10U show the effects of chronic administration of 4-cresol in fat fed mice and Goto-Kakizaki rats on pancreas gene expression. Transcription level of key genes covering various functions relevant to pancreas biology determined by quantitative RT-PCR and the level of NAD and NADH were measured in the total pancreas of C57BL/6J mice fed control chow (CHD) or high fat diet (HFD) (FIGS. 10A-10L) and in Goto-Kakizaki (GK) rats (FIGS. 10M-10U). Results are means±SEM. *$P<0.05$; $P<0.01$; *$P<0.001$; ****$P<0.0001$, significantly different to relevant controls.

Figure 11A:
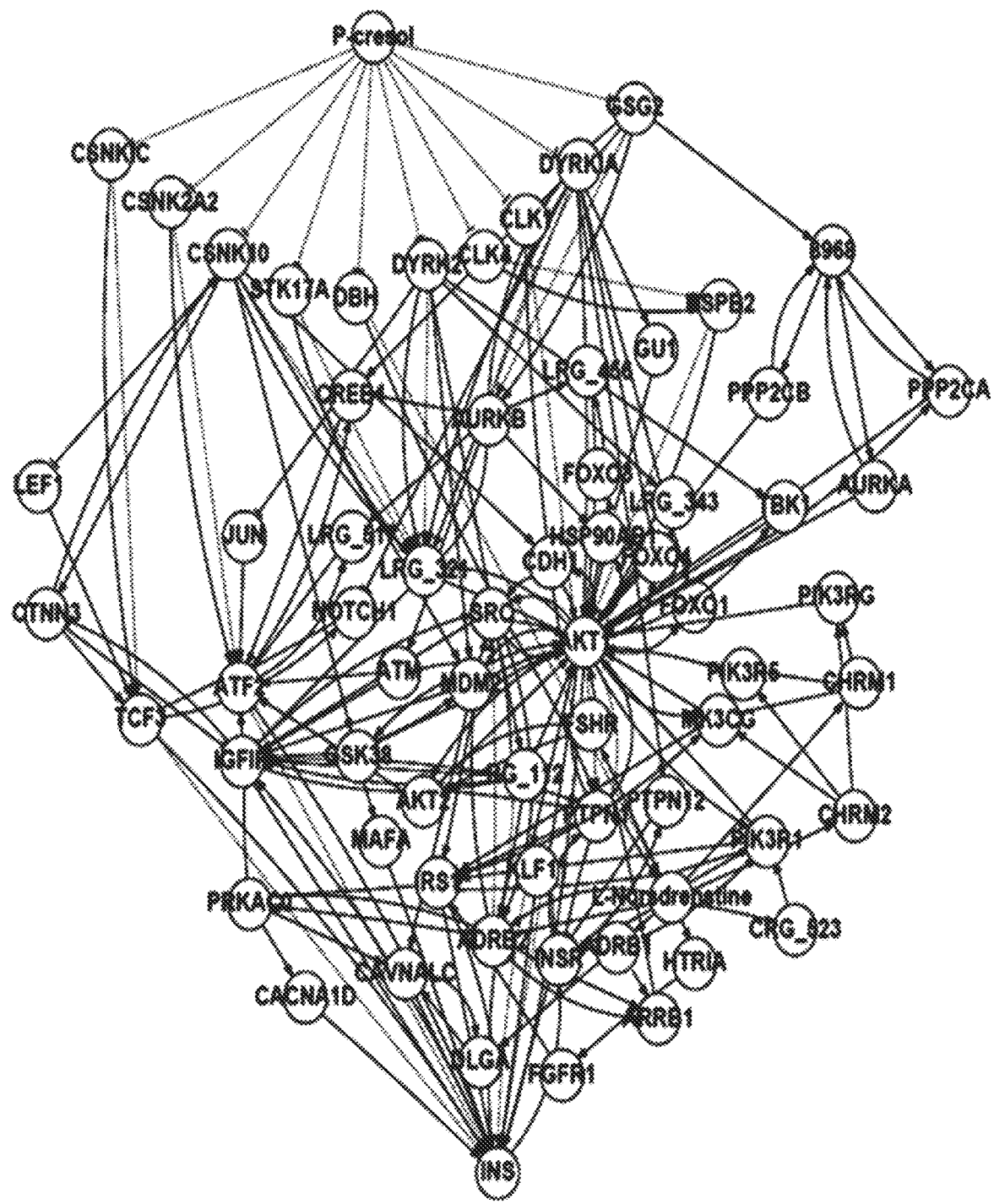
FIGS. 11A-11G show analyses of candidate proteins interacting with 4-cresol.
Figure 11B:
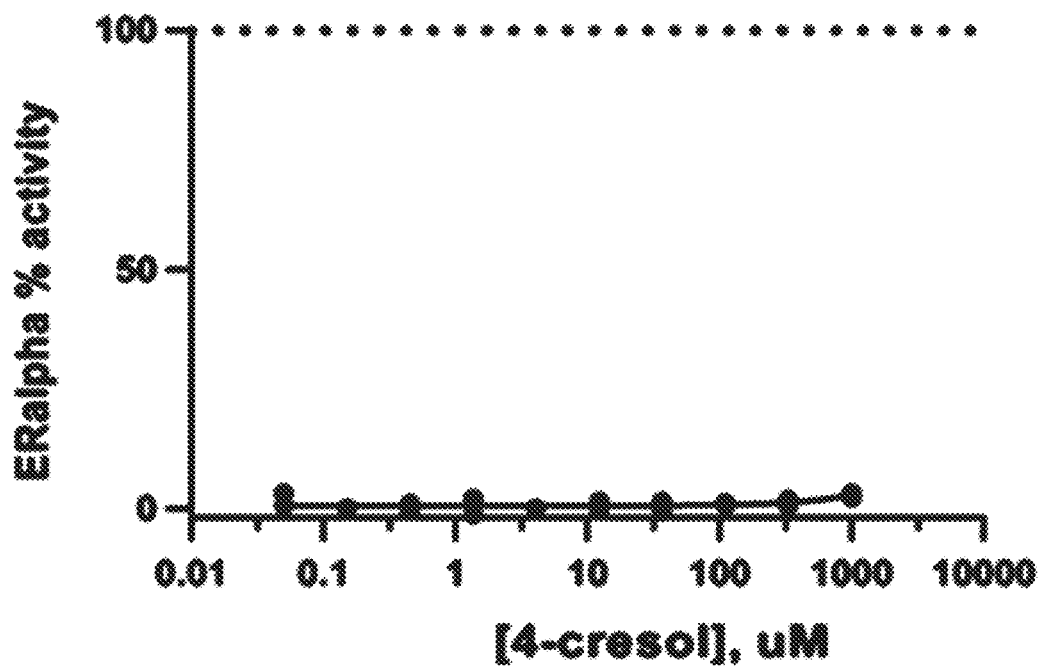
Figure 11C:
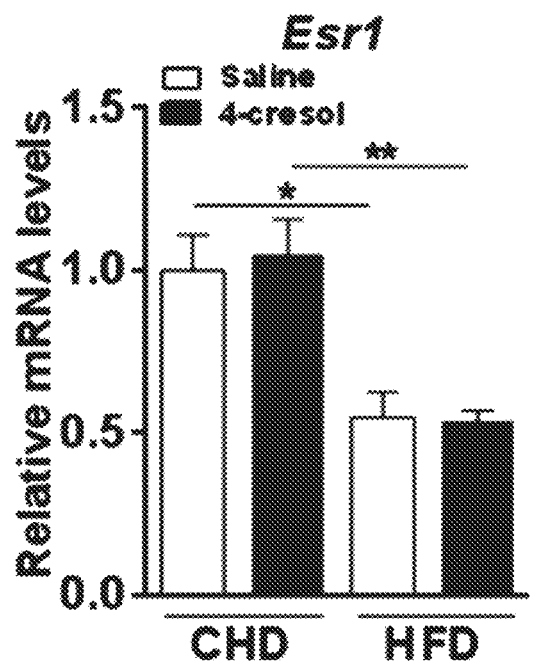
Figure 11D:
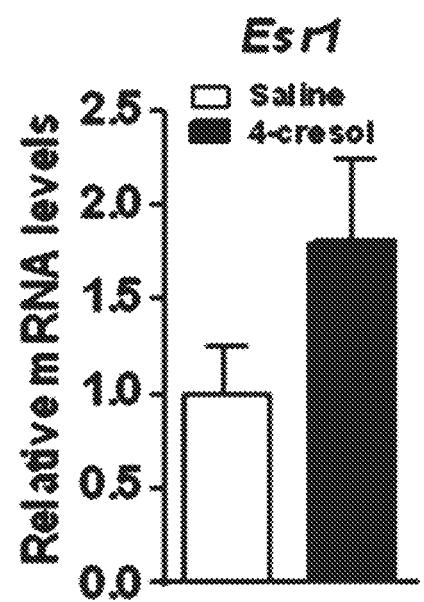
Figure 11E:
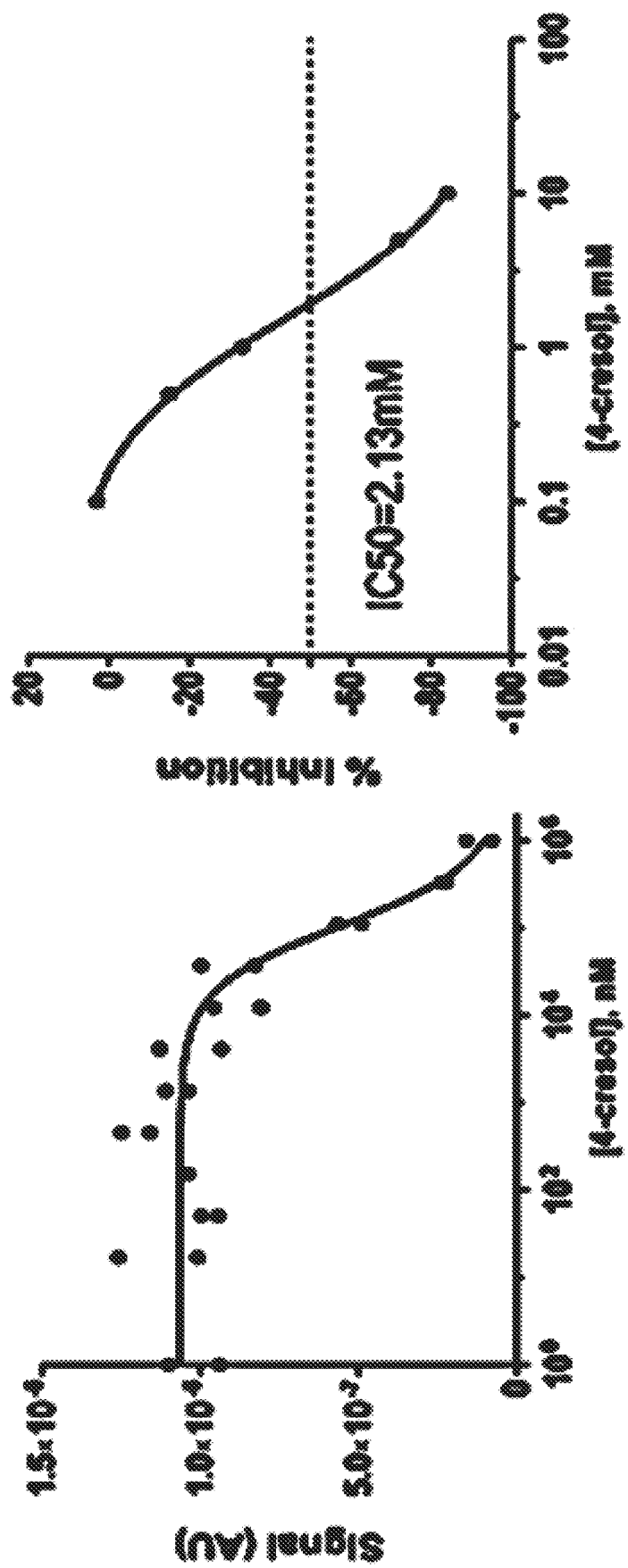
Figures 11F, 11G:
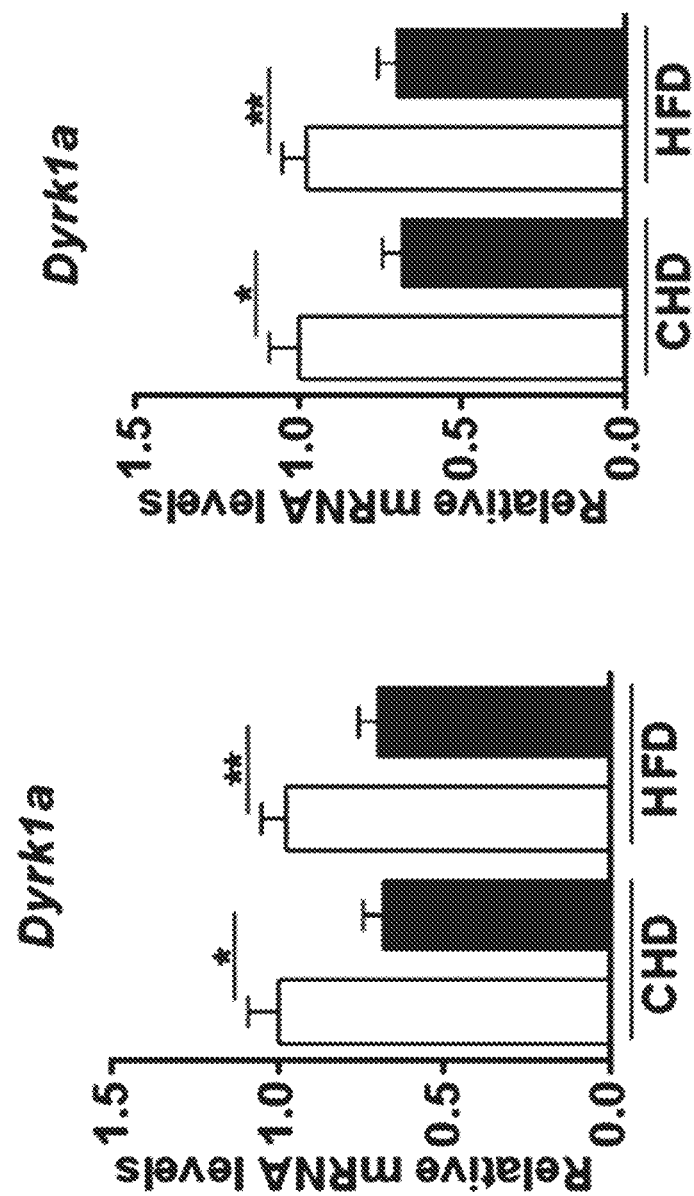

FIGS. 11A-11G show analyses of candidate proteins interacting with 4-cresol. Network was constructed with KEGG (FIG. 11A) and interaction analyses with the estrogen receptor ERα (FIG. 11B) and the dual specificity tyrosine phosphorylation regulated kinase DYRK1α (FIG. 11C) were carried out with DiscoverX. The effect of 4-cresol on transcription of the ERα and DYRK1A was determined by quantitative RT-PCR in pancreas of C57BL/6J mice fed control chow (CHD) or high fat diet (HFD) (FIGS. 11D-11E) and in Goto-Kakizaki (GK) rats (FIG. 11F-11G). Results are means±SEM. *$P<0.05$; **$P<0.01$, significantly different to relevant controls.

FIGS. 12A-12E show the effects of 4-cresol incubation in isolated mouse islets. Insulin release and secretion in response to glucose (FIG. 12A) and insulin content (FIG. 12B) were determined in islets incubated with a control medium and with solutions of 4-cresol 10 nM and 100 nM. Sections of isolated islets treated with a medium free of 4-cresol and with 4-cresol 10 nM and 100M were treated with Ki67 to quantify proliferative nuclei (FIG. 12C, 12D) illustrated in FIG. 12E. Results are means±SEM. *$P<0.05$; $P<0.01$; *$P<0.001$ significantly different between groups.

EXAMPLES

Context and Purpose of the Study

In a prior study of 138 individuals, correlations were found between variations in serum concentrations of a large series of metabolites, which were derived by GC-MS based metabolomic profiling, and coronary stenosis, pathophysiological components of coronary artery disease (as defined by BMI>30 kg/m2, plasma HDL cholesterol concentration <40 mg/dL and fasting hyperglycemia >125 mg/dL) and serum cholesterol.

Among these metabolites, 4-cresol, showed a potentially beneficial effect on CAD risk. The study described hereafter aimed at investigating the biological role of 4-cresol and its potential therapeutic effect on metabolic diseases.

Material and Methods

Animal Experiments

Six weeks-old C57BL/6J male mice (Janvier Labs, Courtaboeuf, France) were received and acclimated in specific pathogen free (SPF) maintenance condition. Mice had free access to a standard chow diet (R04-40, Safe, Augy, France) and were kept on 12 h light/dark cycle. After one week, a group of 12 mice was fed control carbohydrate diet (CHD) (D 12450Ki, Research diets, NJ) and a group of 12 mice was fed high fat (60% fat and sucrose) diet (HFD) (D12492i, Research diets, NJ). One week later mice were anaesthetized with isoflurane and osmotic minipumps Alzet®model 2006 (Charles River Lab France, l'Arbresle, France) filled with the bacterial metabolites 4-cresol or 4-methylcatechol (6 CHD-fed and 6 HFD-fed mice for per metabolite group) (5.55 mM in 0.9% NaCl) (Sigma Aldrich, St Quentin, France) or with saline (6CHD-fed and 6HFD-fed mice) were inserted subcutaneously on the dorsal left side. Concentration of 4-cresol was adjusted for a flow rate of 0.15 µl/h.

The animal experiments on rats were conducted on diabetic adult 8 months aged male Goto-Kakizaki (GK) rats from the local colony of Paris-Diderot University (Paris, France). GK strain derived after backcrossing of animals selected at the upper limit of normal distribution for glucose tolerance. Characteristics of GK rats have been previously described. Rats had free access to a control carbohydrate diet (CHD) (D 12450Ki, Research diets, NJ) and were kept on 12 h light/dark cycle. As for mice, one week later rats were anaesthetized with isoflurane and osmotic minipumps Alzet® model 2006 (Charles River Lab France, l'Arbresle, France) filled with the bacterial metabolites 4-cresol (6 animals 0.2 M in 0.9% NaCl) (Sigma Aldrich, St Quentin, France) or with saline (5 rats) were inserted subcutaneously on the dorsal left side. Concentration of 4-cresol was adjusted for a flow rate of 0.15 µl/h. Rats were killed by decapitation and blood and organs collected for measurement of metabolic parameters, islet isolation for quantitative RT-PCR analysis and immunohistochemistry.

Blood glucose and body weight were monitored weekly during the 6-week long administration of 4-cresol or saline. After three weeks of metabolite treatment (i.e. four weeks of HFD feeding) an intra-peritoneal glucose tolerance test (IPGTT) (2 g/kg) was performed in conscious mice following an overnight fast. Blood was collected from the tail vein before glucose injection and 15, 30, 60 and 120 minutes afterwards. Additional blood samples were collected during the IPGTT in GK rats 15, 90, 180 and 240 minutes after glucose injection. Blood glucose levels were determined using an Accu-Check® Performa (Roche Diagnostics, Meylan, France). Additional blood samples were collected at base line and 30 minutes after glucose injection in Microvette® CB 300 Lithium Heparin (Sarstedt, Marnay, France). Plasma was separated by centrifugation and stored at −80° C. until insulin radioimmunoassay. Evaluation of overall glucose tolerance was obtained from cumulative glycemia (GCum) and the ΔG, which were determined by the total increment of plasma glucose values during the IPGTT (GCum) and the cumulative glycemia during the test above baseline (ΔG). After six weeks of metabolite treatment, mice were killed by decapitation and organ were dissected and weighed. Half of liver, fat and pancreas samples were snap frozen in liquid nitrogen and stored at −80° C. for molecular studies, and the second half processed for histopathology. All procedures were authorized following review by the institutional ethic committee and carried out under national license condition (Ref 00486.02).

Analytical Assays

Blood glucose was measured using an Accu-Check® Performa (Roche Diagnostics, Meylan, France) and plasma insulin was determined using Insulin ELISA kits (Mercodia, Uppsala, Sweden). For determination of liver triglycerides, liver samples (100 mg) were homogenized and incubated in NonidetP-40 (5%) and supernatants containing triglycerides were collected. Triglycerides concentration was quantified in the supernatant fraction using a colorimetric assay (ab65336, Abcam, Paris, France) by measuring OD at 570 nm. The ratio NAD/NADH was determined using a quantification kit (MAK037; SigmaAldrich, St Quentin, France) on extracts prepared from 20 mg pancreas tissue. Samples were homogenized in the extraction buffer and clarified by centrifugation. Supernatant was deproteinized by filtration through a 10-kDa cutoff spin filter (Millipore SAS, Molsheim, France). The assay was then performed according to the manufacturer's instructions.

RNA Isolation and Quantitative RT-PCR

RNA was extracted from pancreas, adipose tissue and liver using the RNeasy RNA Mini Kit (Qiagen, Courtaboeuf, France). Reverse transcription was performed from a 20 μL reaction mixture with 500 ng RNA using M-MLV reverse transcriptase kit (ThermoFisher, Villebon, France). Quantitative RT-PCR was performed using sequence specific primers and the MESA green kit for SYBR green assays (Eurogentec, Angers, France). We used 18S and/or cyclophilin house keeping genes to normalize relative quantification of mRNA levels using the Livak and Scmittgen methods (Livakand Schmittgen, 2001).

Histology and Immunohistochemistry of Mouse Tissues

Tissues were drop-fixed in 4% paraformaldehyde (Sigma-Aldrich, Saint Quentin Fallavier, France) immediately after collection and put through an automated carousel processor for dehydration, clearing, and paraffin embedding (Leica, Nanterre, France). Sections were prepared for liver (6 μm), pancreas (6 μm) and adipose tissue (10 m) and mounted on slides (DPX polymerizing mountant, Sigma-Aldrich, Saint Quentin Fallavier, France). Hematoxylin and Eosin (H&E) was used to evaluate tissue morphology. Epitope-specific antibodies were used for immunohistochemistry detection of insulin on pancreas sections (Dako, Saint Aubin, France).

For Oil redO (ORO), livers were snap frozen in OCT (VWR, Fontenay-sous-Bois, France) and cut into 7-μm sections using a cryostat. Sections were rehydrated in PBS (Sigma-Aldrich, St Quentin, France) and incubated with an ORO staining solution (Sigma Aldrich, St Quentin, France). Slides were washed in deionized water and mounted with Vectashield mounting medium (Laboratoires Eurobio Abcys, LesUlis, France).

For immunohistochemistry analysis, pancreas sections were quenched with 3% H2O2, washed with TBS+0.1% (v/v) Tween-20 (or 0.05% v/v Triton X-100 for nuclear epitopes), blocked with TBS+3% (w/v) BSA and incubated with diluted primary antibodies and then with HRP-conjugated secondary antibody (Bio-Rad, Marnes-la-Coquette, France). Chromogenic detection was carried out with the DAB chromogen kit (Dako, Saint Aubin, France). Nuclei were counterstained with hematoxylin. Quantitative expression of all immunostainings was performed using positive pixels algorithm (Indica Labs, Corrales, N. Mex.). For double immunostaining and immunofluorescence analyses, pancreas sections were stained for insulin as described above and co-stained with i) primary Anti-Ki67 antibody (ab15580, Abcam, Paris, France) and secondary Donkey Anti-Goat IgG H&L conjugated to Alexa Fluor® 568 (ab175704, Abcam, Paris, France) ii) primary Mouse/Rat CD31/PECAM-1 Antibody (AF3628, Minneapolis, USA) and secondary Goat anti-Rabbit IgG H&L conjugated to Alexa Fluor 488 (A-11034, ThermoFisher, Villebon, France). Results are expressed as percentage of positive pixels, within islets where indicated. The quantification method is an automated observer-independent process based on section scanning and application of publicly available algorithms. Each biological replicate represents one slide per animal mounted with at least 3 tissue sections, representing 3 technical replicates, the mean and variance of which is presented as the result per biological replicate. All images were acquired on an Axiovert 200M microscope (Zeiss, Marly-le-Roi, France).

Results

4-Cresol Treatment Improves Glucose Homeostasis and Reduces Body Growth

To test the biological role of microbial metabolites in vivo we focused experimental validation analyses of human data on 4-cresol, which showed a beneficial effect on BMI. Mice fed control diet or HFD were chronically treated with subcutaneous infusion of 4-cresol 0.04M (0.5 mg/kg/day) for 42 days. Subcutaneous treatment was preferred over dietary supplementation or oral gavage in order to control permanent delivery of 4-cresol over a long period of time, reduce the stress induced by animal handling and avoid possible toxic effects of this volatile compound observed at much higher doses (240-2000 mg/kg/day) on neurological function, liver function and respiratory epithelium (Andersen, 2006). As expected, mice fed HFD rapidly gained more weight than mice fed control diet and developed fasting hyperglycemia and marked glucose intolerance (FIG. 1A-1F). Glycemia after the glucose challenge, cumulative glycemia during the test and the ΔG parameter were significantly more elevated in mice fed HFD than in controls (FIG. 1C-1F). Fasting insulin and glucose-induced insulin secretion were not significantly affected by HFD (FIG. 1G).

Chronic infusion of mice fed control diet with 4-cresol resulted in progressive reduction in body weight when compared to mice treated with saline (FIG. 1A). This effect became significant after 4 weeks of 4-cresol treatment and remained significant until the end of the experiment when it was associated with a significant decrease in BMI (FIG. 1B). Glucose tolerance was improved by 4-cresol, as indicated by the significant reduction in both acute glycemic response to the glucose challenge and cumulative glycemia during the IPGTT when compared to saline-treated mice (FIG. 1C, 1D). 4-cresol infusion resulted in a significant increase in glucose-stimulated insulin secretion when compared to controls (FIG. 1G).

The effect of 4-cresol on body weight, glycemic control and insulin secretion was also strongly significant in HFD-fed mice (FIG. 1A-1G). In addition, 4-cresol treatment in fat fed mice induced strong reduction in fasting glycemia (FIG. 1F) and in the $\Delta G$ parameter, which was normalized to the level of mice fed chow diet and treated with saline (FIG. 1E), and fasting hyperinsulinemia (FIG. 1G) when compared to HFD-fed mice infused with saline.

In Vivo 4-Cresol Treatment Alters Organ Weight and Reduces Liver Triglycerides

To further characterize the effects of 4-cresol on CMD relevant phenotypes, organ weight and liver triglycerides content were measured in the mouse groups. After seven weeks of HFD, mice exhibited significantly elevated adiposity, which was calculated as the ratio of the weight of adipose tissue (retroperitoneal fat pads) to body weight (FIG. 1H) and reduced heart weight (FIG. 2) when compared to mice fed chow diet. Liver triglycerides levels were markedly increased by HFD but this effect was not statistically significant (FIG. 1K). In both diet groups, chronic administration of 4-cresol over 6 weeks resulted in significant reduction in adiposity index (FIG. 1H) and increased pancreas weight by 48.9% (FIG. 1I) when compared to mice treated with saline. Heart and kidney weight were not affected by 4-cresol (FIG. 2). Liver weight was reduced in HFD-fed mice treated with 4-cresol (FIG. 1J). 4-cresol treatment resulted in a systematic and dramatic reduction in liver triglycerides content in both diet groups (FIG. 1K).

Collectively, these data demonstrate the beneficial effects of chronic administration of 4-cresol in vivo in mice on obesity, and extend the characterization of its beneficial effects on improved glucose tolerance and reduced triglycerides in the liver.

Chronic 4-Methylcatechol Treatment Mimics Biological Effects of 4-Cresol.

To investigate both the sensitivity of in vivo biological systems to the stimulation by 4-cresol and the physiological role of its potential microbial products, the phenotypic screening was repeated in mice treated with 4-methylcatechol (4-MC), which is structurally related to 4-cresol. 4-MC is a bacterial product of 4-cresol through enzymatic reactions potentially involving mono-oxygenase, dioxygenase and cycloisomerase (Kolomytseva et al., 2007). Chronic treatment with 4-MC in mice fed chow diet or HFD induced a strong reduction in body growth and BMI (FIG. 3A, 3B), significant improvement in glycemic control on both diets, as reflected by improved glucose tolerance (FIG. 3C) and reduced fasting glycemia, cumulative glycemia and $\Delta G$ (FIGS. 3D-3F), and increased insulin secretion (FIG. 3G) when compared to mice treated with saline. Treatment of mice fed HFD or control diet with 4-MC induced significant reduction in adiposity, liver weight and liver triglycerides and increased pancreas weight (FIG. 3H-3K). These results indicate that 4-cresol and 4-MC regulate the same biological mechanisms in several tissues.

Chronic 4-Cresol Treatment Alters Histology Features in Adipose Tissue and Liver To characterize the effects of 4-cresol on adiposity at the cellular level, we carry out adipose tissue histology in the four mouse groups (FIG. 4A-4D). Consistent with increased adiposity in response to fat feeding, HFD feeding induced a strongly significant 84.8% increase in adipocyte size (56.27±0.47 in CHD fed mice and 104.00±1.41 in HFD fed mice) (FIG. 4A, 4B).

Occurrence of liver structural lesions resembling nonalcoholic fatty liver disease (NAFLD) is a phenotypic hallmark consistently observed in mice fed HFD in our experimental conditions (Dumas et al., 2006). To investigate the effect of 4-cresol on these defects and test the structural relevance of reduced liver triglycerides observed in mice treated by 4-cresol (FIG. 1K), we carried out liver histology in the four mouse groups. HFD feeding induced a strongly significant 4.27-fold increase in liver fat content determined by Oil-Red-O staining of liver sections (FIG. 4C, 4D). In response to 4-cresol infusion, liver fat content was reduced in mice fed CHD, and also strongly reduced by 40.7% in HFD fed mice (P=0.009) to the level of saline-treated CHD-fed controls (FIG. 4D).

Gene Expression Changes Induced by Chronic 4-Cresol Treatment in Adipose Tissue

To investigate molecular changes potentially underlying morphological changes in adipose tissue caused by 4-cresol treatment, the expression of a selection of genes known to regulate adipocyte function in obesity was analyzed (FIG. 5). Expression of sirtuin 1 (Sirt1), caveolin 2 (Cav2), hormone-sensitive lipase (Hsl) and patatin-like phospholipase domain containing 2 (Pnpla2, Atg1) was significantly stimulated by 4-cresol in CHD fed mice, whereas uncoupling protein 1 (Ucp1) expression was markedly downregulated (FIG. 5A-F). Expression of Hsl and Pnpla2 remained significantly upregulated by 4-cresol in HFD-fed mice when compared to saline treated fat fed mice, and Ucp1 was significantly downregulated in these mice when compared to both HFD-fed mice treated with saline and CHD-fed mice treated with 4-cresol.

Chronic 4-Cresol Administration Promotes Cell Proliferation and Increases Pancreatic Vascularization and Islet Density Following the observation that 4-cresol had strong effect on pancreas weight in both diet groups, this phenomenon was investigated further through with histology and gene expression analyses. To test whether islet structure was affected by 4-cresol, we focused histopathology analyses on islets in sections stained by HE. Fat feeding did not significantly affect insulin positive area (58.95±11.75 in CHD fed mice; 109.03±24.15 in HFD fed mice, P=071) (FIG. 6A, 6B), but increased islet density (FIG. 6C, 6D). 4-cresol administration was associated with a strong increase in both islet density and insulin positive area in mice fed CHD (185.40±22.95) or HFD (171.90±21.62), but the effect was statistically significant only in CHD-fed mice. We noted that islets in pancreas sections of cresol treated mice were predominantly located in the close vicinity of the vasculature (FIG. 6C), suggesting an effect of 4-cresol on enhanced islet neogenesis.

We then used KI67 to determine pancreatic cell proliferation in the four mouse groups. The number of proliferative nuclei was increased in HFD-fed mice when compared to CHD-fed mice (FIG. 7A-7C). Immunohistochemistry confirmed elevated islet size 4-cresol treated mice (153.60±14.18 in CHD fed mice; 170.00±12.56 In HFD fed mice) when compared to CHD-fed mice treated with saline (50.81±2.90) (FIG. 7A, 7B). The number of proliferative nuclei was increased in HFD-fed mice when compared to CHD-fed mice (FIG. 7A-7C). It was also significantly increased in response to 4-cresol treatment in CHD-fed mice and remained elevated in HFD-fed mice. Increased vascularization from endothelial cells contributes to pancreatic cell proliferation and islet neogenesis, and may explain the effect of 4-cresol on cell proliferation. To test this hypothesis, we then stained pancreas section of the four mouse groups with CD31, which is a marker of vascularization. The number of CD31 positive cells was significantly increased in response to HFD (FIG. 7D, 7E). In both groups fed CHD or HFD, 4-cresol induced a further significant increase in CD31 positive cells, thus demonstrating the role of this metabolite on the stimulation of pancreas vascularization.

Collectively, these results illustrate the wide spectrum of pancreatic histological features and mechanisms affected by in vivo 4-cresol chronic administration, which may account for its effects on increased pancreas weight, enhanced glucose-stimulated insulin secretion in vivo and improved glucose tolerance in a model of obesity and insulin resistance induced experimentally.

Figures 12A, 12B:
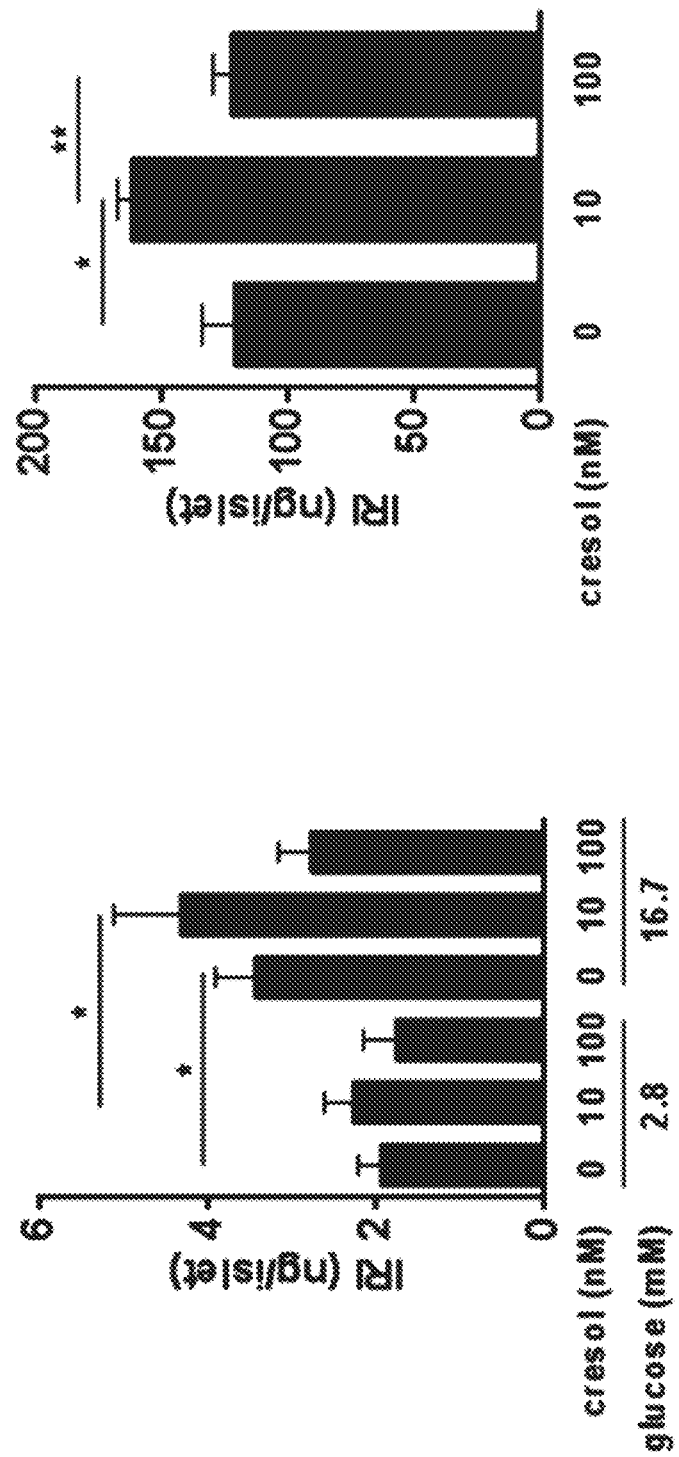
FIGS. 12A-12E show the effects of 4-cresol incubation in isolated mouse islets.
Figure 12D:
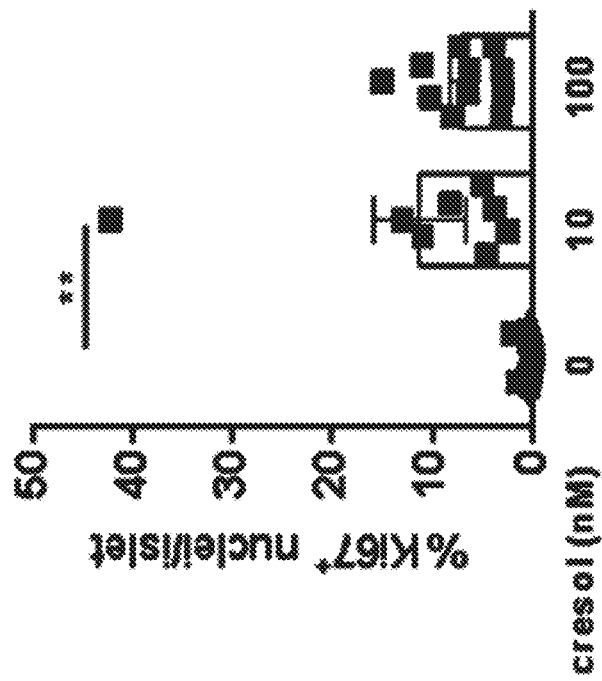
Figure 12C:
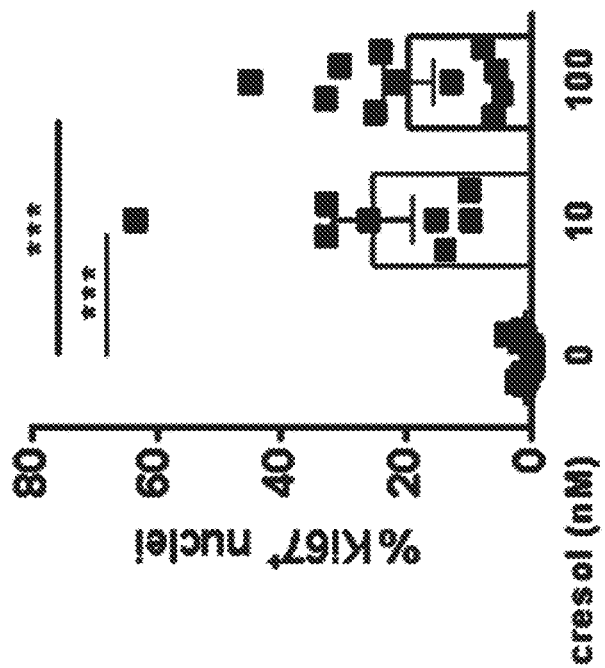
Figure 12E:
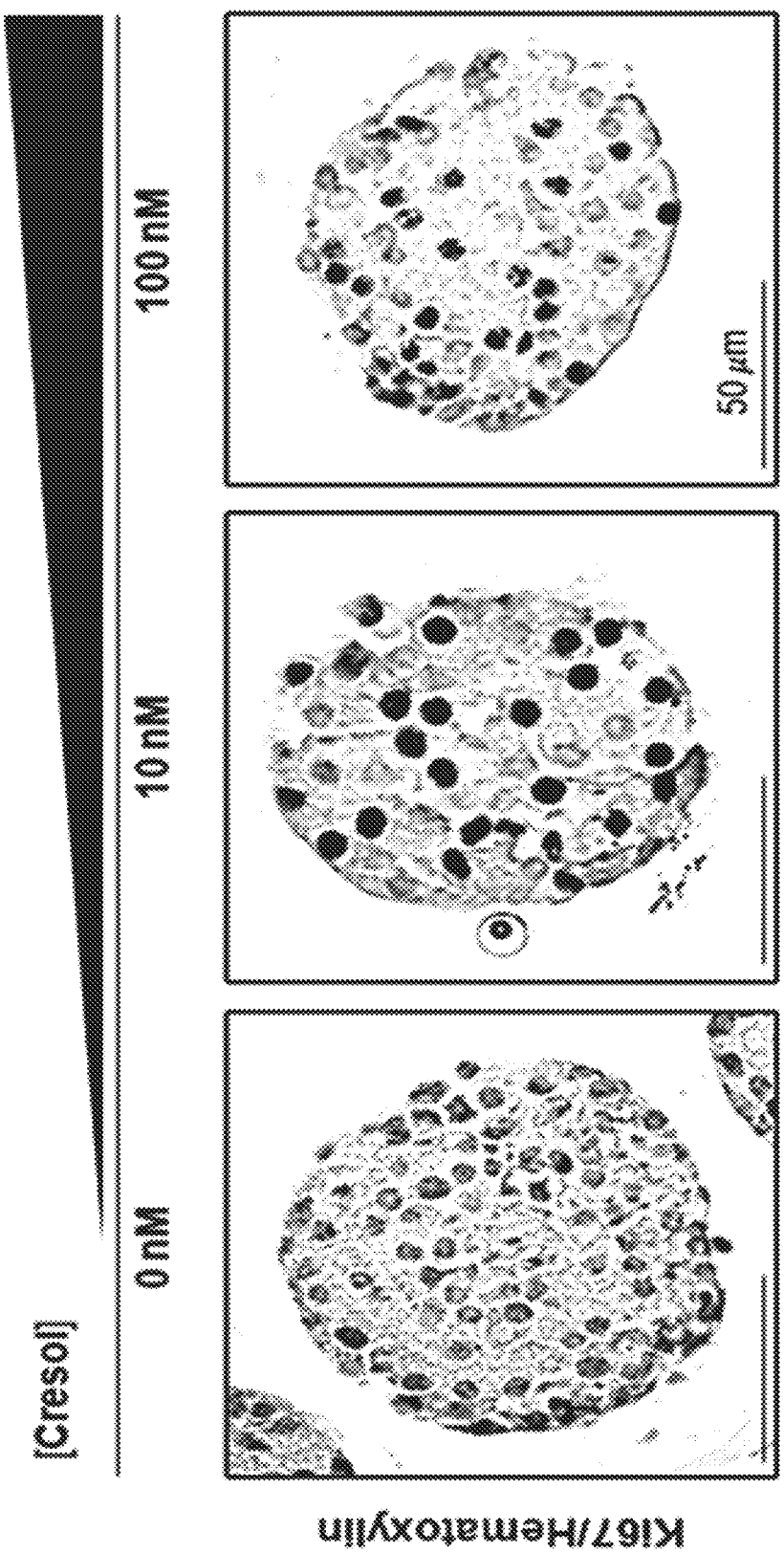

4-Cresol Stimulates Insulin Content and Cell Proliferation in Isolated Mouse Islets To confirm the functional role of 4-cresol in pancreatic islets, we incubated islets isolated from mice with a concentration of 4-cresol (10 nM) corresponding to the dose administered in vivo in mice, and a higher dose (100 nM). The lower dose of 4-cresol induced a strong increase in insulin release under basal condition (2.8 mM glucose) (+17.3%), a marked stimulation of insulin secretion in response to glucose 16.6 mM (+25.8%, p=0.06) (FIG. 12A), and a significant increase in islet insulin content (+33.7%, p<0.05) (FIG. 12B). Incubation with 4-cresol at 100 nM had no effect on insulin production, secretion and content. Labeling of islets with KI67 revealed a significant effect of 4-cresol 10 nM on islet cell proliferation (FIG. 12C, 12D), as illustrated in FIG. 12E. These results demonstrate the role of 4-cresol on beta cell function in vitro, and corroborate in vivo data in mice treated chronically with 4-cresol.

4-Cresol Treatment Improves Glucose Homeostasis and Boosts Insulin Secretion and Islet Density in the Goto-Kakizaki Rat We next sought whether the effects of 4-cresol on improved insulin secretion and pancreas cell proliferation in a model of diet-induced diabetes can be replicated in a situation of spontaneous deterioration of glucose homeostasis and islet structure. We used the model of genetically determined diabetes in the Goto-Kakizaki (GK) rat, which was produced through repeated breeding out bred Wistar rats over many generations using glucose intolerance for selecting breeders (Bihoreau et al., 2017). Chronic administration of 4-cresol had no effect on body weight and BMI (FIG. 8). In contrast, adiposity index was significantly reduced, even though the GK is not a model of obesity, and pancreas weight nearly doubled (+94.6%, P<0.01) in 4-cresol treated rats (FIG. 8). This effect of 4-cresol was associated with a significant reduction in fasting glycemia, in glucose intolerance reflected by a decrease in the glycemic response to the glucose challenge throughout the IPGTT, as reflected by the significant drop in cumulative glycemia (FIG. 9A-9C). Fasting insulinemia and glucose-induced insulin secretion during the IPGTT were significantly more elevated in GK treated with 4-cresol than in rats treated with saline (FIG. 9D). Pancreas histology analyses showed a significant increase in insulin positive area in response to 4-cresol, which was associated with increased cell proliferation determined by Ki 67 labeling (FIG. 9E-9G).

These results strongly support data obtained in HFD-fed mice and demonstrate that 4-cresol administration dramatically improves diabetes phenotypes in a model characterized by spontaneously occurring insulin deficiency and deteriorated islet structure.

4-Cresol Chronic Treatment is Associated with Profound Changes in Pancreas Gene Expression To get insights into molecular mechanisms that may contribute to structural and functional changes induced by 4-cresol in the pancreas, expression of selected genes covering various aspects of pancreas biology was tested by quantitative RT-PCR in HFD-fed and control mice (FIGS. 10A-10L) and in GK rats (FIG. 10M-10U). Expression of uncoupling protein 2 (Ucp2), interleukins (IL6, IL10) and tumor necrosis factor (Tnf) was increased by HFD feeding. Chronic treatment by 4-cresol in CHD-fed mice led to increased transcription of genes encoding amylase, vascular endothelial growth factor (Vegf), brain derived neurotrophic factor (Bdnf), IL10 and Sirt1, which coincided with increased NAD/NADH ratio, when compared to saline-treated CHD-fed mice. Enhanced expression of the insulin gene (Ins1) and the transcription factor HNF1 homeobox A (Hnf1α) by 4-cresol and reduced expression of Ucp2 in this comparison were not statistically significant. In mice fed HFD 4-cresol induced significant overexpression of genes encoding Sirt1 and Ins1, and significantly reduced expression of Ucp2, IL6 and Tnf when compared to HFD-fed mice treated with saline. IL10 transcript level remained elevated in HFD-fed mice treated with 4-cresol. Bndf, Hnf1α, Pdx1 and Vegf were also strongly overexpressed in response to 4-cresol in these mice but differences to 4-cresol treated mice fed HFD were not statistically significant.

The stimulatory effects of 4-cresol chronic administration on the expression of Sirt1, Ins1, Hnf1α, IL10 and Vegfa were replicated in GK pancreas (FIG. 10M-10U). Expression of genes encoding amylase, IL6 and Tnf was strongly altered in 4-cresol treated GK rats, but differences to GK rats treated with saline were not statistically significant.

These results demonstrate the broad ranging molecular consequences of 4-cresol treatment in the pancreas of animal models of diabetes induced experimentally by dietary changes or caused by naturally occurring genetic polymorphisms.

Pancreatic Expression of DYRK1A is Stimulated by 4-Cresol Chronic Administration In Vivo.

To explain the amelioration of pancreatic function by 4-cresol in the diabetic models tested, we investigated possible candidate signaling mechanisms mediating its effects in the pancreas. Due to the chemical properties of 4-cresol, which is a phenol-related metabolite, we hypothesized that 4-cresol involves signaling pathways similar to those mediating the cellular action of polyphenols (eg. resveratrol, harmine) known to stimulate β-cell formation (estrogen receptor ERα) and proliferation (dual specificity tyrosine phosphorylation regulated kinase DYRK1A). We initially carried out network analysis, which showed that several kinases, including DYRK1A mediate the effects of 4-cresol on insulin secretion (FIG. 11A). We then tested experimentally using in vitro systems the interaction between 4-cresol and ERα and DYRK1A by determination of the EC50. We found that 4-cresol does not interact with ERα (FIG. 11B), but does bind DYRK1A (FIG. 11C). 4-cresol does not regulate significantly the pancreatic expression of ERα in fat fed mice and GK rats in vivo (FIG.

11D, 11E). In contrast, we observed a significant downregulation of DYRK1A pancreatic transcription in both mice fed control or HFD and GK rats treated chronically with 4-cresol (FIG. 11F, 11G).

CONCLUSION

The effects of chronic administration of 4-cresol in vivo in mice did validate prior findings that this metabolite has a negative correlation with obesity in humans.

Most importantly, data obtained demonstrated that 4-cresol can have beneficial effects on glycemic control, insulin secretion and obesity. It provided evidence for its broad ranging roles in improved glucose regulation, enhanced insulinemia and glucose-induced insulin secretion, reduced liver triglycerides and possibly islet neogenesis. These results further suggest that 4-cresol and 4-MC are ligands that may bind the same cellular signaling mediators with low specificity and may affect the same biological pathways.

Results from gene expression analysis in adipose tissue and pancreas provide insights into molecular mechanisms underlying physiological and histological features caused by in vivo administration of 4-cresol. Overexpression of Hsl, Pnpla2 (Atg1) and Sirt1, and consequent Ucp1 downregulated expression, in adipose tissue of mice treated with 4-cresol indicates stimulated lipolysis and inhibited lipogenesis, and accounts for reduced adiposity in these mice. Gene expression data in pancreas suggest that 4-cresol contributes to reduce inflammation, as illustrated by stimulated expression of IL10 and downregulated expression of both IL6 and Tnf, and to increase both vascularisation and parasympathetic tone through upregulated expression of Vegf and Bdnf, respectively. Of note, Bdnf reduces hyperglycemia and increases the number and area of pancreatic islets in diabetic db/db mice (Yamanaka et al., 2006). Downregulated expression of Ucp2 and increased NAD+/NADH ratio in the pancreas of mice treated with 4-cresol can be explained by upregulated expression of Sirt1. The multiple functional roles of Sirt1 on stimulation of insulin secretion, reduction of adipogenesis, liver lipid accumulation and inflammation, and improvement of glucose homeostasis (Liang et al., 2009) suggests that it could be a central regulatory node in the pathophysiological effects of 4-cresol.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

REFERENCES

Andersen, A. (2006). Final report on the safety assessment of sodium p-chloro-m-cresol, p-chloro-m-cresol, chlorothymol, mixed cresols, m-cresol, o-cresol, p-cresol, isopropyl cresols, thymol, o-cymen-5-ol, and carvacrol. Int J Toxicol 25 Suppl 1, 29-127.

Bihoreau, M. T., Dumas, M. E., Lathrop, M. & Gauguier, D. Genomic regulation of type 2 diabetes endophenotypes: Contribution from genetic studies in the Goto-Kakizaki rat. *Biochimie* (2017).

Cummings, J. H. (1983). Fermentation in the human large intestine: evidence and implications for health. Lancet 1, 1206-1209.

Dumas, M. E., Barton, R. H., Toye, A., Cloarec, O., Blancher, C., Rothwell, A., Fearnside, J., Tatoud, R., Blanc, V., Lindon, J. C., et al. (2006). Metabolic profiling reveals a contribution of gut microbiota to fatty liver phenotype in insulin-resistant mice. Proc Natl AcadSci USA 103, 12511-12516.

Hansen, T. H., Gøbel, R. J., Hansen, T., and Pedersen, 0. (2015). The gut microbiome in cardio-metabolic health. Genome Med 7, 33.

Kolomytseva, M. P., Baskunov, B. P., and Golovleva, L. A. (2007). Intradiol pathway of para-cresol conversion by Rhodococcusopacus 1CP. Biotechnol J 2, 886-893.

Le Chatelier, E., Nielsen, T., Qin, J., Prifti, E., Hildebrand, F., Falony, G., Almeida, M., Arumugam, M., Batto, J. M., Kennedy, S., et al. (2013). Richness of human gut microbiome correlates with metabolic markers. Nature 500, 541-546.

Liang, F., Kume, S., and Koya, D. (2009). SIRT1 and insulin resistance. Nat Rev Endocrinol 5, 367-373.

Nicholson, J. K., Holmes, E., and Wilson, I. D. (2005). Gut microorganisms, mammalian metabolism and personalized health care. Nat Rev Microbiol 3, 431-438.

Qin, J., Li, Y., Cai, Z., Li, S., Zhu, J., Zhang, F., Liang, S., Zhang, W., Guan, Y., Shen, D., et al. (2012). A metagenome-wide association study of gut microbiota in type 2 diabetes. Nature 490, 55-60.

Yamanaka, M., Itakura, Y., Inoue, T., Tsuchida, A., Nakagawa, T., Noguchi, H., and Taiji, M. (2006). Protective effect of brain-derived neurotrophic factor on pancreatic islets in obese diabetic mice. Metabolism 55, 1286-1292.

The invention claimed is:

1. A method of treatment of a condition selected from glucose intolerance related conditions selected from the group consisting of pre-diabetes, insulin-dependent diabetes mellitus (type 1 diabetes mellitus), non-insulin-dependent diabetes mellitus (type 2 diabetes mellitus), gestational diabetes mellitus, insulin deficit related conditions, nonalcoholic fatty liver disease, and obesity, comprising administering to an individual in need thereof a therapeutically effective amount of a compound of formula (I)

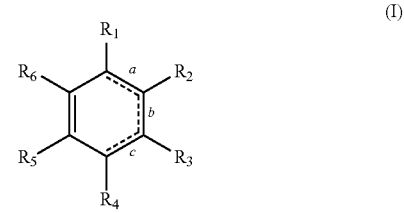

wherein
$R_1$ represents a C1-C4 alkyl group, —C(=O)H, or —CH$_2$—CH(COOH)—CH$_2$—COOH,
$R_2$ represents —H or —CH$_3$;
$R_3$ represents —H;
$R_4$ represents —OH;
$R_5$ represents —H or —CH$_3$; and
$R_6$ represents —H, or —CH$_3$, a and c represent a double bond, and b represents a single bond;

one of its pharmaceutically acceptable salts, or a composition comprising the compound of formula (I) or pharmaceutically acceptable salts thereof.

2. The method as defined in claim 1, wherein said compound is chosen from the list consisting of 4-cresol, 4-hydroxybenzylsuccinate, and 4-hydroxybenzaldehyde.

3. The method as defined in claim 1, wherein said compound is 4-cresol.

4. The method as defined in claim 1, wherein the condition is type 1 diabetes mellitus.

5. The method as defined in claim 1, wherein the condition is pre-diabetes, pre-diabetes with impaired fasting glucose, pre-diabetes with impaired glucose tolerance, type 2 diabetes mellitus, or gestational diabetes mellitus.

6. The method as defined in claim 1, wherein the compound is administered through the parenteral route via intravenous, intramuscular, subcutaneous or intradermal administration.

7. The method as defined in claim 1, wherein the compound is administered by injection or infusion.

8. The method as defined in claim 1, wherein $R_1$ represents —$CH_3$.

* * * * *

UNITED STATES PATENT AND TRADEMARK OFFICE
CERTIFICATE OF CORRECTION

| | | |
|---|---|---|
| PATENT NO. | : 11,491,117 B2 | Page 1 of 1 |
| APPLICATION NO. | : 16/652947 | |
| DATED | : November 8, 2022 | |
| INVENTOR(S) | : D. Gauguier et al. | |

It is certified that error appears in the above-identified patent and that said Letters Patent is hereby corrected as shown below:

On the Title Page

Item (72) Inventors After the last inventor, insert:
-- Pierre Zalloua, Zouk Mikael (LB) --.

Signed and Sealed this
Sixth Day of May, 2025

Coke Morgan Stewart
*Acting Director of the United States Patent and Trademark Office*